US010047357B2

(12) United States Patent
Short

(10) Patent No.: US 10,047,357 B2
(45) Date of Patent: *Aug. 14, 2018

(54) SIMULTANEOUS, INTEGRATED SELECTION AND EVOLUTION OF ANTIBODY/PROTEIN PERFORMANCE AND EXPRESSION IN PRODUCTION HOSTS

(71) Applicant: BioAtla, LLC, San Diego, CA (US)

(72) Inventor: Jay Milton Short, Del Mar, CA (US)

(73) Assignee: BIOATLA, LLC, San Diego, CA (US)

( * ) Notice: Subject to any disclaimer, the term of this patent is extended or adjusted under 35 U.S.C. 154(b) by 523 days.

This patent is subject to a terminal disclaimer.

(21) Appl. No.: 14/481,564

(22) Filed: Sep. 9, 2014

(65) Prior Publication Data

US 2015/0024944 A1 Jan. 22, 2015

Related U.S. Application Data

(62) Division of application No. 13/384,362, filed as application No. PCT/US2010/042302 on Jul. 16, 2010, now Pat. No. 8,859,467.

(60) Provisional application No. 61/271,168, filed on Jul. 17, 2009.

(51) Int. Cl.
*C40B 30/04* (2006.01)
*C12N 15/10* (2006.01)
*C07K 16/00* (2006.01)
*C40B 50/06* (2006.01)

(52) U.S. Cl.
CPC .......... *C12N 15/1058* (2013.01); *C07K 16/00* (2013.01); *C40B 50/06* (2013.01); *C07K 2317/21* (2013.01); *C07K 2317/52* (2013.01); *C40B 30/04* (2013.01)

(58) Field of Classification Search
None
See application file for complete search history.

(56) References Cited

U.S. PATENT DOCUMENTS 3,817,837 A 6/1974 Rubenstrin et al.
3,850,752 A 11/1974 Wiljelmus et al.
3,939,350 A 2/1976 Kronick et al.
(Continued)

FOREIGN PATENT DOCUMENTS

EP 0329822 8/1988
EP 2454376 B1 12/2015
(Continued)

OTHER PUBLICATIONS

Yang et al. (1995) Journal of Molecular Biology vol. 254 pp. 392 to 403.*
(Continued)

*Primary Examiner* — Christian C Boesen
(74) *Attorney, Agent, or Firm* — Mendelsohn Dunleavy, P.C.

(57) ABSTRACT

The present disclosure provides methods of integrating therapeutic protein and antibody generation and/or selection, evolution and expression in a eukaryotic host for manufacturing in a single system. Therapeutic proteins, including antibodies, are generated, optimized and manufactured in the same eukaryotic host system. The disclosed system of Comprehensive Integrated Antibody Optimization (CIAO!™) allows for simultaneous evolution of protein performance and expression optimization.

14 Claims, 7 Drawing Sheets

(56) References Cited

U.S. PATENT DOCUMENTS

| | | | |
|---|---|---|---|
| 3,996,345 | A | 12/1976 | Ullman et al. |
| 4,196,265 | A | 4/1980 | Koprowski et al. |
| 4,275,149 | A | 6/1981 | Litman et al. |
| 4,277,437 | A | 7/1981 | Maggio |
| 4,366,241 | A | 12/1982 | Tom et al. |
| 4,683,195 | A | 7/1987 | Mullis et al. |
| 4,683,202 | A | 7/1987 | Mullis |
| 4,800,159 | A | 1/1989 | Mullis et al. |
| 4,883,750 | A | 11/1989 | Whiteley et al. |
| 5,677,149 | A | 10/1997 | Bauer et al. |
| 6,171,820 | B1 | 1/2001 | Short |
| 6,562,594 | B1 | 5/2003 | Short |
| 6,764,835 | B2 | 7/2004 | Short |
| 7,790,655 | B2 | 9/2010 | Gao et al. |
| 7,947,495 | B2 | 5/2011 | Dubridge et al. |
| 2003/0219752 | A1 | 11/2003 | Short |
| 2006/0115850 | A1 | 6/2006 | Schatz |
| 2007/0128203 | A1 | 6/2007 | Giles-Komar |

FOREIGN PATENT DOCUMENTS

| | | |
|---|---|---|
| GB | 2202328 | 9/1988 |
| WO | WO8706270 | 10/1987 |
| WO | WO8906700 | 7/1989 |
| WO | WO8909284 | 10/1989 |
| WO | WO02066514 | 8/2002 |
| WO | WO02092780 A2 | 11/2002 |
| WO | WO03023032 A2 | 3/2003 |
| WO | WO05003345 A2 | 1/2005 |
| WO | WO07047578 A2 | 4/2007 |
| WO | WO2009061369 A2 | 5/2009 |

OTHER PUBLICATIONS

Georgescu et al. (1992) Methods in Molecular Biology vol. 231 pp. 75 to 83.*

Australian Patent Examination Report: dated Jan. 6, 2015 for the corresponding AU Application No. AU2010273974.

European Examination Report; dated Jan. 28, 2015 for the corresponding EP Application No. 10 800 618.0.

Miao, H.Z., et al., "Bioengineering of Coagulation Factor VIII for Improved Secretion," Blood Journal, May 1, 2004, vol. 103, No. 9, pp. 3412-3420.

Mexican Office Action; dated Feb. 20, 2015 for the corresponding MX Application No. MX/2014/064203.

Non-Final Office Action; dated Jan. 16, 2015 for the corresponding U.S. Appl. No. 13/298,559.

Chinese Office Action; dated Apr. 1, 2015 for the corresponding CN Application No. CN201080038839.4 inclusive of an English abstract.

European Search Report; dated May 8, 2015 for the corresponding EP Application No. 15156820.1.

Boder, E., et al., "Yeast Surface Display for Screening Combinatorial Polypeptide Libraries," Nature Biotechnology, vol. 15, No. 6, 1997, pp. 553-557.

Böhm, Ernst, et al. "Screening for improved cell performance: selection of subclones with altered production kinetics or improved stability by cell sorting." Biotechnology and bioengineering 88.6 (2004): 699-706.

Rader, Christoph, David A. Cheresh, and Carlos F. Barbas. "A phage display approach for rapid antibody humanization: designed combinatorial V gene libraries." Proceedings of the National Academy of Sciences 95.15 (1998): 8910-8915.

Vajdos, Felix F., et al. "Comprehensive functional maps of the antigen-binding site of an anti-ErbB2 antibody obtained with shotgun scanning mutagenesis." Journal of molecular biology 320.2 (2002): 415-428.

Suckow, Jörg, et al. "Genetic studies of the lac repressor XV: 4000 single amino acid substitutions and analysis of the resulting phenotypes on the basis of the protein structure." Journal of molecular biology 261.4 (1996): 509-523.

Famm, Kristoffer, et al. "Thermodynamically stable aggregation-resistant antibody domains through directed evolution." Journal of molecular biology 376.4 (2008): 926-931.

Non-Final Office Action: dated Jun. 22, 2015 for the related U.S. Appl. No. 13/298,559.

Japanese Notice of Reasons for Refusal; dated Apr. 19, 2016 for JP Application No. JP2015-094521.

Japanese Pre-Trial Patentability Report; dated Apr. 18, 2016 for JP Application No. JP2016-002569.

Korean Office Action; dated Jun. 17, 2016 for Korean Application No. KR1020127003948.

Mexican Office Action; dated Oct. 27, 2016 for MX Application No. MX/A/2012/000803.

Australian Search Report; dated Nov. 18, 2016 for AU Application No. AU2015243076.

European Office Action; dated Feb. 9, 2017 for EP Application No. EP16157965.1.

European Search Report; dated Feb. 3, 2017 for EP Application No. EP16196481.2.

Chinese Notification of Reexamination; dated Feb. 10, 2017 for CN Application No. CN201080038839.4.

JP Final Decision of Rejection; dated Jan. 30, 2017 for JP Application No. JP2015-094521.

Chinese Office Action; dated Sep. 18, 2014 for corresponding CN Application No. 201080038839.4 along with English abstract.

Wu, H., et al., "Stepwise In Vitro Affinity Maturation of Vitaxin, an $\alpha v \beta 3$-specific humanized mAb," Proceedings of the National Academy of Sciences of the United States of America, vol. 95, No. 11 (May 26, 1998), pp. 6037-6042.

Ho, M., et al., "Isolation of Anti-CD22 Fv with High Affinity by Fv Display on Human Cells," Proceedings of the National Academy of Sciences of the United States of America, vol. 103, No. 25 (Jun. 20, 2006), pp. 9637-9642.

Akamatsu, Y., et al., "Whole IgG surface display on mammalian cells: Application to isolation of neutralizing chicken monoclonal anti-IL-12 antibodies," Journal of Immunological Methods, vol. 327, Issues 1-2, Oct. 31, 2007, pp. 40-52.

Kawahara, M., et al., "Reversal of antigen-dependent signaling by two mutations in antibody/receptor chimera: implication of inverse agonism in cytokine receptor superfamily," Biochemical Pharmacology, vol. 68, Issue 3, Aug. 1, 2004, pp. 539-548.

Notice of Reasons for Refusal; dated Nov. 4, 2014 for corresponding JP Application No. 2012-520813.

Rajpal, A., et al., "A general method for greatly improving the affinity of antibodies by using combinatorial libraries," Proceedings of the National Academy of Sciences US, vol. 102, No. 24, Jun. 1, 2005, pp. 8466-8471.

Iba, Y., et al., "Expression vectors for the introduction of highly diverged sequences into the six complementarity-determining regions of an antibody," Gene, Elsvier, Amsterdam, NL, vol. 194, No. 1, Jul. 18, 1997, pp. 35-46.

European Search Report; dated Jun. 7, 2013 for corresponding EP Application No. EP10800618.0.

Singapore Written Opinion; dated Nov. 14, 2013 for the related SG Application No. 2012003356/131114/TMSAH/5475.

English Translation of Mexican Office Action; dated Feb. 13, 2014 for MX Application No. MX/a/2012/000803.

Chinese Office Action; dated Aug. 6, 2013 for corresponding CN Application No. 201080038839.4.

Zhong, Y., et al., "Identification and Expression of Human ScFv Against Surface Antigen of Hepatitis B Virus in *E. Coli*," Virologica Sinica, vol. 16, No. 2, pp. 105-108, 2001.

Chinese Office Action; dated Apr. 6, 2014 for the corresponding CN Application No. 201080038839.4 with an English Abstract.

Mexican Office Action; dated Jun. 23, 2014 for the related Mexican Application No. MX/a/20121000803.

Schlatter et al. (Nov. 16, 2004) Biotechnoloty Progress, vol. 21, pp. 122-133.

Int'l. Search Report and Written Opinion for Int'l Application No. PCT/US10/42302, dated Feb. 11, 2011.

Rakenstraw, et al., Biotechnology Progress, Jul. 6, 2006, vol. 22, pp. 1200-1208.

(56) References Cited

OTHER PUBLICATIONS

Boder, et al., Proceedings of the National Academy of Sciences USA, vol. 97, pp. 10701-10705, Sep. 26, 2000.
File History for U.S. Appl. No. 13/298,559 through Sep. 30, 2014.
File History for U.S. Appl. No. 13/384,362 through Sep. 30, 2014.
European Search Report; dated May 8, 2015 for the corresponding EP Application No. 16157965.1.
Chinese Reexamination Decision; dated Sep. 21, 2017 for CN Application No. 201080038839.4.
EP Office Action; dated Oct. 17, 2017 for EP Application No. 16196481.2.
KR Office Action; dated Jun. 29, 2017 for KR Application No. KR10-2012-7003948.
Non-Final Office Action; dated Nov. 29, 2017 for U.S. Appl. No. 13/298,559.
Korean Notice of Submission of Opinion; dated Apr. 16, 2018 for KR Application No. 10-2018-7002028.
Oswald, N., "Choosing a Competent *E.coli* Strain," 2017, as retrieved from: https://bitesizebio.com/10292/choosing-a-competent-ecoli-strain/, 5 pages.
Jäger, Volker, et al. "High level transient production of recombinant antibodies and antibody fusion proteins in HEK293 cells." BMC biotechnology 13.1 (2013): 52.
Steger, K., et al., "Literature Review: CHO Versus HEK Cell Glycosylation," 2015 as retrieved from: https://www.maxcyte.com/application_note_tec/literature-review-cho-versus-hek-cell-glycosylation/.
Indian Examination Report; dated Nov. 16, 2017 for in Application No. 737/DELNP/2012. Examination Report is in both Indian and English.

* cited by examiner

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Synthetic sequence used as a linker between a
      VH domain and a VL domain in a single-chain antibody. This linker
      may be repeated two or more times.

<400> SEQUENCE: 1

Gly Gly Gly Gly Ser
1               5
```

SIMULTANEOUS, INTEGRATED SELECTION AND EVOLUTION OF ANTIBODY/PROTEIN PERFORMANCE AND EXPRESSION IN PRODUCTION HOSTS

This application is a division of U.S. Non-Provisional application Ser. No. 13/384,362, filed Mar. 5, 2012; which is a 371 of International Patent Application Serial No. PCT/US10/42302, filed Jul. 16, 2010, which claims priority to U.S. Provisional Application No. 61/271,168, filed Jul. 17, 2009, the entire contents of which are incorporated herein by reference.

FIELD OF THE INVENTION

In a particular aspect, the present invention is relevant to proteins and to their optimization by protein evolution. Protein therapeutics are discovered, evolved and manufactured in the same host using the same genetic systems.

BACKGROUND OF THE INVENTION

A variety of antibody and other protein systems that generate candidate protein therapeutic molecules have been designed, developed and implemented. More recently, many evolution systems have been developed to enhance the function of the proteins. Separately, mammalian expression systems have been developed for high yield production of antibodies and other proteins for therapeutic applications. To date, no group has developed a system to enable the generation, evolution of an antibody or protein, and protein production/manufacturing in a single efficient mammalian expression system.

Many antibodies are developed using bacteria phage display systems in bacteria, while expression of full-length antibodies is carried out primarily in mammalian cells. This lack of similarity makes evolution or selection of clones for expression impossible. Additional barriers include the traditional requirement for large numbers of variants to be screened using traditional technologies and high level mammalian expression systems have been optimized for expression, not cloning of large numbers of variants. An integrated antibody/protein selection, evolution and mammalian expression system has not previously been designed. The use of surface display in mammalian cells for handling large numbers, combined with non-stochastic evolution of the antibody/protein inside of an optimized mammalian host cell, increases the likelihood of success and greatly accelerates the process for generating an optimized antibody/protein that will express at high enough levels in mammalian cells desired in manufacturing.

SUMMARY OF THE INVENTION

The present disclosure provides methods of integrating therapeutic protein (including antibodies) generation and/or selection, evolution and expression in a eukaryotic host, such as a mammalian cell host or a yeast cell host, for manufacturing in a single system. Therapeutic proteins, including antibodies, are generated, optimized and manufactured in the same eukaryotic host system. The disclosed system of Comprehensive Integrated Antibody Optimization (CIAO!™) allows for simultaneous evolution of protein performance and expression optimization.

In one embodiment the disclosure provides a method of selection, evolution and expression of an antibody in a mammalian cell production host; the method comprising generating an anti-antigen antibody library in a mammalian cell production host with antibody cell surface display; screening the library for at least one predetermined property, characteristic or activity; selecting a template antibody from the library; evolving the template antibody to produce a set of mutant antibodies in the mammalian cell production host with antibody cell surface display; screening the mutant antibodies for the at least one predetermined property, characteristic or activity; selecting an up-mutant antibody from the set of mutant antibodies based upon optimization of the at least one predetermined property, characteristic or activity when compared to the template antibody; and expressing the up-mutant antibody in the same mammalian cell production host as used in the generating step. In one aspect, the antigen is pre-selected. In another aspect, the anti-antigen antibody library is a humanized anti-antigen antibody library.

In one aspect, the mammalian cell production host is selected from 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; *S. cerevisiae* yeast cells; or *picchia* yeast cells. In a particular aspect, the mammalian system is CHO-S or HEK293. In one aspect, the screening steps utilize fluorescence-activated cell sorting (FACS).

In another aspect, the evolving step comprises producing a set of mutant antibodies formed from the template antibody having m complementary determining regions (CDR), wherein m is an integer selected from 1, 2, 3, 4, 5 or 6, each said CDR comprising n amino acid residues, the method comprising generating m×n separate sets of antibodies, each set comprising member antibodies having X number of different predetermined amino acid residues at a single predetermined position of the CDR; wherein each set of antibodies differs in the single predetermined position; and the number of different member antibodies generated is equivalent to m×n×X. In a particular aspect, m is 6.

In one aspect, the evolving step comprises generating n−1 separate sets of mutant polypeptides from the template antibody, each set comprising member polypeptides having X number of different predetermined amino acid residues at a single predetermined position of the polypeptide; wherein each set of polypeptides differs in the single predetermined position; and the number of different member polypeptides generated is equivalent to [n−1]×X. In one aspect, X represents the 19 naturally occurring amino acid residues not present in a given position of the template polypeptide.

In another aspect, the screening step comprises assaying each member polypeptide for at least one predetermined property, characteristic or activity; identifying any change in said property, characteristic or activity of the member polypeptide relative to the template polypeptide; creating a functional map wherein the functional map is used to identify positions and mutations in the mutant polypeptide which result in an up-mutant and/or a silent mutation compared to the template polypeptide.

In another aspect, the functional map is used to identify one or more of the group consisting of (a) positions and mutations which do not affect the activity of the mutant polypeptide compared to the template polypeptide; (b) fully mutable sites compared to the template polypeptide; and (c)

positions and mutations which result in an up-mutant compared to the template polypeptide.

In another aspect, the antibody fragment is selected from a heavy chain, light chain, variable domain, constant domain, hypervariable region, complementarity determining region 1 (CDR1), complementarity determining region 2 (CDR2), and complementarity determining region 3 (CDR3).

In another aspect, the generating step comprises subjecting a codon-containing polynucleotide encoding for said template polypeptide to polymerase-based amplification using a 64-fold degenerate oligonucleotide for each codon to be mutagenized, wherein each of said 64-fold degenerate oligonucleotides is comprised of a first homologous sequence and a degenerate N,N,N triplet sequence, so as to generate a set of progeny polynucleotides; and subjecting said set of progeny polynucleotides to clonal amplification such that polypeptides encoded by the progeny polynucleotides are expressed.

The method of claim 1 wherein the predetermined property, characteristic or activity is selected from reduction of protein-protein aggregation, enhancement of protein stability, increased protein solubility, introduction of glycosylation sites, introduction of conjugation sites, reduction of immunogenicity, enhancement of protein expression, increase in antigen affinity, decrease in antigen affinity, change in binding affinity, change in immunogenicity, or enhancement of specificity.

In another embodiment, the disclosure provides a method of evolution and expression of an antibody in a mammalian cell production host; the method comprising selecting a template antibody; evolving the template antibody to produce a set of mutant antibodies in a mammalian cell production host with antibody cell surface display; screening the mutant antibodies for the at least one predetermined property, characteristic or activity; selecting an up-mutant antibody from the set of mutant antibodies based upon optimization of the at least one predetermined property, characteristic or activity compared to the template antibody; and expressing the up-mutant antibody in the same mammalian cell production host used in the evolving step.

In one aspect, the screening step comprises creating a functional map wherein the functional map is used to identify positions and mutations in the mutant polypeptide which result in an up-mutant and/or a silent mutation compared to the template polypeptide. In another aspect, the screening steps comprise fluorescence-activated cell sorting (FACS).

In one aspect, the mammalian cell production host is selected from 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; and PER C.6, human embryonic cells. In a particular aspect, the mammalian system is CHO-S or HEK293. In another aspect, the cell production host is selected from CHOK1SV or NS0 host cell lines.

In another embodiment, the disclosure provides a method of evolution and expression of a protein in a eukaryotic cell production host; the method comprising selecting a template antibody; evolving the template antibody to produce a set of mutant antibodies in a eukaryotic cell production host; screening the mutant antibodies for at least one predetermined property, characteristic or activity; selecting an up-mutant antibody from the set of mutant antibodies based upon optimization of the at least one predetermined property, characteristic or activity compared to the template antibody; and expressing the up-mutant antibody in the same eukaryotic cell production host as in the evolving step for any commercial scale.

In one embodiment, the disclosure provides a method of evolution and manufacturing of a human protein in a cell production host; the method comprising generating a human protein library in a cell production host selected from one of the group consisting of a bacterial or eukaryotic production host; screening the library for at least one predetermined property, characteristic or activity; selecting a template human protein from the library based upon the at least one predetermined property, characteristic or activity; evolving the template human protein to produce a set of mutant human proteins in the cell production host; screening the set of mutant human proteins for the at least one predetermined property, characteristic or activity and screening for modified expression; selecting an up-mutant human protein from the set of mutant human proteins based upon (1) optimization of the at least one predetermined property, characteristic or activity and (2) modified expression when compared to the template human protein; and manufacturing the human protein comprising expressing the up-mutant human protein in the same production host as in the generating step. In one aspect, the modified expression in the selecting step is improved expression.

In another aspect, the evolving step comprises an evolution technique selected from one of comprehensive positional evolution (CPE); comprehensive positional insertion evolution (CPI); comprehensive positional deletion evolution (CPD); comprehensive positional evolution (CPE) followed by combinatorial protein synthesis (CPS); comprehensive positional deletion evolution (CPD) followed by combinatorial protein synthesis (CPS); or comprehensive positional deletion evolution (CPD) followed by combinatorial protein synthesis (CPS).

In one aspect, the human protein is an antibody. In another aspect, the antibody is a full length antibody.

In another aspect, the at least one predetermined property, characteristic or activity in screening step (e) comprises one or more of (1) screening for a silent mutation and (2) screening for a missense mutation; compared to the template antibody.

In another aspect, one or more portions of the antibody selected from Fc and Fv; framework; and one or more CDRs are modified in the up-mutant human antibody compared to the template human antibody is evolved.

In another aspect, the screening step comprises screening the set of mutant human proteins for the at least one predetermined property, characteristic or activity and screening for modified expression simultaneously.

In a further aspect, the human protein for evolution and manufacturing is selected from an enzyme cytokine, receptor, DNA binding protein, chelating agent or hormone.

In another aspect, the cell production host is a eukaryotic production host and the evolving step comprises evolving the template human protein to produce a set of mutant human proteins in the eukaryotic cell production host with cell surface display.

In another embodiment, the disclosure provides a method of evolution for enhanced expression and manufacturing of a human protein in a eukaryotic cell production host; the method comprising selecting a template human protein for evolution; evolving the template human protein comprising generation of mutant codons encoding the template human protein to produce a set of mutant human proteins in the production host; screening the set of mutant human proteins for at least one predetermined property, characteristic or activity and screening for enhanced expression when compared to the template human protein; selecting an up-mutant human protein from the set of mutant human proteins based upon (1) retention or optimization of the at least one predetermined property, characteristic or activity and (2) enhanced expression when compared to the template human protein; and manufacturing the up-mutant human protein comprising expressing the up-mutant human protein in the same production host as in the evolving step.

In one aspect, the mutant codons of the up-mutant human protein result in at least one silent mutation and/or missense mutation. In another aspect, the mutant codons of the up-mutant human protein result in at least one silent mutation.

In a further aspect, the template human protein is an approved ethical protein therapeutic drug, and the up-mutant human protein is a biosimilar.

In another aspect, the selecting step comprises selecting an up-mutant human protein from the set of mutant human proteins based upon (1) optimization of the at least one predetermined property, characteristic or activity and (2) enhanced expression when compared to the template human protein.

In another embodiment, the disclosure provides a method of identifying and producing a target human protein, the method comprising generating an human protein library in a eukaryotic cell production host with protein cell surface display; screening the library for at least one predetermined property, characteristic or activity; identifying a target human protein from the library based upon the at least one predetermined property, characteristic or activity; and expressing the target human protein in the same eukaryotic cell production host as in the generating step to produce a target human protein. In one aspect, the target human protein is an antibody. In another aspect, the antibody is a full length antibody.

In another embodiment, the disclosure provides a method of evolution of a human protein in a manufacturing host, the method comprising mutating a template human protein to produce a set of mutant human proteins in a manufacturing host; and screening the set of mutant progeny proteins for at least one predetermined property, characteristic or activity. In one aspect, the method further comprises selecting an up-mutant human protein from the set of mutant human proteins based upon the at least one predetermined property, characteristic or activity. In another aspect, the method further comprises manufacturing the up-mutant human protein comprising expressing the up-mutant human protein in the same production host as in the mutating step. In another aspect, the selecting step further comprises selecting an up-mutant human protein from the set of mutant human proteins based upon (1) optimization of the at least one predetermined property, characteristic or activity when compared to the template human protein, and (2) modified expression when compared to the template human protein. In one aspect, the modified expression is enhanced expression.

In another embodiment, the disclosure provides a method of evolution and manufacturing of a human protein in a cell manufacturing host; the method comprising mutating a template human protein to produce a set of mutant human proteins in a manufacturing host; screening the set of mutant human proteins for at least one predetermined property, characteristic or activity and screening for modified expression; selecting an up-mutant human protein from the set of mutant human proteins based upon (1) optimization of the at least one predetermined property, characteristic or activity, and (2) modified expression when compared to the template human protein; and manufacturing the human protein comprising expressing the up-mutant human protein in the same manufacturing host as in the mutating step.

In a further embodiment, the disclosure provides a method of evolution for enhanced expression and manufacturing of a human protein in a eukaryotic cell production host; the method comprising mutating a template human protein comprising generation of mutant codons encoding the template human protein to produce a set of mutant human proteins in a manufacturing host; screening the set of mutant human proteins for at least one predetermined property, characteristic or activity and screening for enhanced expression when compared to the template human protein; selecting an up-mutant human protein from the set of mutant human proteins based upon (1) retention or optimization of the at least one predetermined property, characteristic or activity and (2) enhanced expression when compared to the template human protein; and manufacturing the up-mutant human protein in the same manufacturing host as in the mutating step.

In one aspect, the screening step comprises screening the set of mutant human proteins for the at least one predetermined property, characteristic or activity and screening for enhanced expression simultaneously.

DEFINITION OF TERMS

Figure 1:
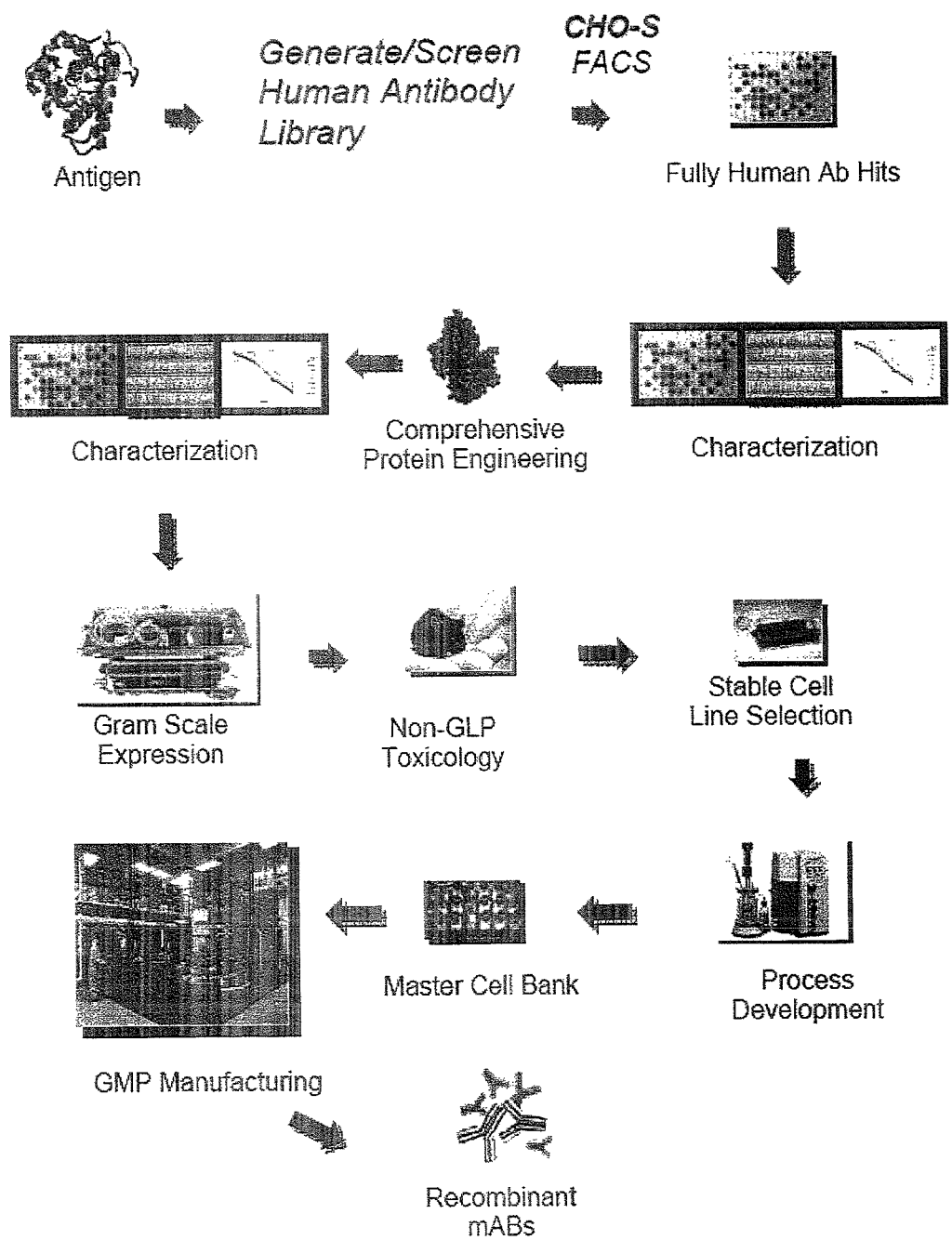
FIG. 1 provides a schematic of the CIAO!™ method of integrating therapeutic protein (e.g., antibody) generation and/or selection, evolution and expression in a eukaryotic host, such as a mammalian cell host or a yeast cell host, for manufacturing in a single system.

In order to facilitate understanding of the examples provided herein, certain frequently occurring methods and/or terms will be described.

The term "agent" is used herein to denote a polypeptide, a mixture of polypeptides, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made form biological materials such as bacteria, plants, fungi, or animal (particular mammalian) cells or tissues. Agents are evaluated for potential activity as anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA") is a genetically engineered single chain molecule containing the variable region of a light chain and the variable region of a heavy chain, linked by a suitable, flexible polypeptide liner.

The term "biosimilar", also termed "follow-on biologic", refers to officially approved new versions of innovator biopharmaceutical products, following patent or exclusivity expiry.

The term "cell production host", or "manufacturing host", refers to a cell line used for the production or manufacturing of proteins. Eukaryotic cells such as mammalian cells, including, but not limited to human, mouse, hamster, rat, monkey cell lines as well as yeast, insect and plant cell lines. Prokaryotic cells can alternatively be utilized. In one aspect, a mammalian cell production host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells. In another aspect, the cell production host is a GS-NS0 or GS-CHOK1 cell line. In another aspect, the cell production host is selected from *S. cerevisiae* yeast cells; and *picchia* yeast cells. In another aspect, the cell production host is a bacterial cell line.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "commercial scale" means production of a protein or antibody at a scale appropriate for resale.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482 by the homology alignment algorithm of Needlemen and Wuncsch J. Mol. Biol. 48: 443 (1970), by the search of similarity method of Pearson and Lipman Proc. Natl. Acad. Sci.

(U.S.A.) 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia. CDR definitions are also generally known as supervariable regions or hypervariable loops (Chothia and Leks, 1987; Clothia et al., 1989; Kabat et al., 1987; and Tramontano et al., 1990). Variable region domains typically comprise the amino-terminal approximately 105-115 amino acids of a naturally-occurring immunoglobulin chain (e.g., amino acids 1-110), although variable domains somewhat shorter or longer are also suitable for forming single-chain antibodies. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. H means the variable heavy chain and L means the variable light chain. The CDR regions of an Ig-derived region may be determined as described in Kabat (1991). Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The term "comprehensive" is used herein to refer to a technique of evolution wherein every possible change is made at each position of a template polynucleotide or template polypeptide and the polynucleotide or polypeptide is tested to confirm the intended changes have been made.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of enzyme which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of (20)10 sequences, and (2) a pseudorandom 10-mer sequence of the 20 conventional amino acids can be any of (20)10 sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences (NNK)10 and (NNM)10, wherein N represents A, T, G, or C; K represents G or T; and M represents A or C, are defined sequence kernels.

The term "deimmunization" as used herein relates to production of a variant of the template binding molecule, which is modified compared to an original wild type molecule by rendering said variant non-immunogenic or less immunogenic in humans. Deimmunized molecules according to the invention relate to antibodies or parts thereof (like frameworks and/or CDRs) of non-human origin. Corresponding examples are antibodies or fragments thereof as described in U.S. Pat. No. 4,361,549. The term "deimmunized" also relates to molecules, which show reduced propensity to generate T cell epitopes. In accordance with this invention, the term "reduced propensity to generate T cell epitopes" relates to the removal of T-cell epitopes leading to specific T-cell activation.

Furthermore, reduced propensity to generate T cell epitopes means substitution of amino acids contributing to the formation of T cell epitopes, i.e. substitution of amino acids, which are essential for formation of a T cell epitope. In other words, reduced propensity to generate T cell epitopes relates to reduced immunogenicity or reduced capacity to induce antigen independent T cell proliferation. In addition, reduced propensity to generate T cell epitopes relates to deimmunization, which means loss or reduction of potential T cell epitopes of amino acid sequences inducing antigen independent T cell proliferation.

The term "T cell epitope" as used herein relates to short peptide sequences which can be released during the degradation of peptides, polypeptide or proteins within cells and subsequently be presented by molecules of the major histocompatibility complex (MHC) in order to trigger the activation of T cells; see inter alia WO 02/066514. For peptides presented by MHC class II such activation of T cells can then induce an antibody response by direct stimulation of B cells to produce said antibodies.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. DNA shuffling can be random or non-random.

As used in this invention, the term "epitope" refers to an antigenic determinant on an antigen, such as a phytase polypeptide, to which the paratope of an antibody, such as a phytase-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

The term "evolution" refers to a change in at least one property, characteristic or activity of a genetically or synthetically modified protein or antibody when compared to a template protein or antibody.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus, areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "humanized" is used to describe antibodies wherein complementarity determining regions (CDRs) from a mammalian animal, e.g., a mouse, are combined with a human framework region. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. In another aspect, besides mouse antibodies, other species can be humanized, such as, for example, other rodent, camel, rabbit, cat, dog, pig, horse, cow, fish, llama and shark. In a broad aspect, any species that produces antibodies can be utilized in the production of humanized antibodies. Additionally, the antibodies of the invention may be chimeric, human-like, humanized or fully human, in order to reduce their potential antigenicity, without reducing their affinity for their target Chimeric, human-like and humanized antibodies have generally been described in the art. By incorporating as little foreign sequence as possible in the hybrid antibody, the antigenicity is reduced. Preparation of these hybrid antibodies may be carried out by methods well known in the art.

In an alternative aspect, human or mouse antibodies are adapted to a different recipient species, such as an endangered species, in order to provide therapeutics for the recipient species while protecting them from a negative immune response. In this aspect, the frameworks from a recipient species are utilized in combination with CDRs from a known or second species antibodies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," Kabat et al., 1987). The sequences of the framework regions of different light or heavy chains are relatively conserved within a species. As used herein, a "human framework region" is a framework region that is substantially identical (about 85 or more, usually 90-95 or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. In accordance with this invention, a framework region relates to a region in the V domain (VH or VL domain) of immunoglobulins that provides a protein scaffold for the hypervariable complementarity determining regions (CDRs) that make contact with the antigen. In each V domain, there are four framework regions designated PRE FR2, FR3 and FR4. Framework 1 encompasses the region from the N-terminus of the V domain until the beginning of CDR1, framework 2 relates to the region between CDR1 and CDR2, framework 3 encompasses the region between CDR2 and CDR3 and framework 4 means the region from the end of CDR3 until the C-terminus of the V domain; see, inter alia, Janeway, Immunobiology, Garland Publishing, 2001, 5th ed. Thus, the framework regions encompass all the regions outside the CDR regions in VH or VL domains.

The person skilled in the art is readily in a position to deduce from a given sequence the framework regions and, the CDRs; see Kabat (1991) Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The benefits of this invention extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Maniatis et al., 1982, p. 146). Unless otherwise provided, ligation may be accomplished using known buffers and conditions with 10 units of T4 DNA ligase ("ligase") per 0.5 μg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

The term "mammalian cell surface display" refers to a technique whereby a protein or antibody, or a portion of an antibody, is expressed and displayed on a mammalian host cell surface for screening purposes; for example, by screening for specific antigen binding by a combination of magnetic beads and fluorescence-activated cell sorting. In one aspect, mammalian expression vectors are used for simultaneous expression of immunoglobulins as both a secreted and cell surface bound form as in DuBridge et al., US 2009/0136950, which is incorporated herein by reference. In another aspect, the techniques of Gao et al. are employed for a viral vector encoding for a library of antibodies or antibody fragments are displayed on the cell membranes when expressed in a cell as in Gao et al., US 2007/0111260, incorporated herein by reference. Whole IgG surface display on mammalian cells is known. For example, a Akamatsuu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to the form for production of soluble IgG. Akamatsuu et al. J. Immunol. Methods 2007 327(1-2):40-52; incorporated herein by reference. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by a single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. Ho et al. Isolation of anti-CD22 Fv with high affinity by Fv display on human cells, Proc Natl Acad Sci USA 2006 June 20; 103(25): 9637-9642; incorporated herein by reference.

Beerli et al. used B cells specific for an antigen of interest which were directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. This method allows isolating antigen-specific antibodies by a single round of FACS. The variable regions (VRs) of the heavy chains (HCs) and light chains (LCs) were isolated from positive clones and recombinant fully human antibodies produced as whole IgG or Fab fragments. In this manner, several hypermutated high-affinity antibodies binding the Qβvirus like particle (VLP), a model viral antigen, as well as antibodies specific for nicotine were isolated. All antibodies showed high expression levels in cell culture. The human nicotine-specific mAbs were validated preclinically in a mouse model. Beerli et al., Isolation of human monoclonal antibodies by mammalian cell display, Proc Natl Acad Sci USA. 2008 September 23; 105(38): 14336-14341; incorporated herein by reference.

Yeast cell surface display is also known, for example, see Kondo and Ueda 2004, Yeast cell-surface display-applications of molecular display, Appl. Microbiol. Biotechnol., 64(1): 28-40, which describes for example, a cell-surface engineering system using the yeast *Saccharomyces cerevisiae*. Several representative display systems for the expression in yeast *S. cerevisiae* are described in Lee et al, 2003, Microbial cell-surface display, TRENDS in Bitechnol. 21(1): 45-52. Also Boder and Wittrup 1997, Yeast surface display for screening combinatorial polypeptide libraries, Nature Biotechnol., 15(6): 553.

The term "manufacturing" refers to production of a protein at a sufficient quantity to permit at least Phase I clinical testing of a therapeutic protein, or sufficient quantity for regulatory approval of a diagnostic protein.

The term "missense mutation" refers to a point mutation where a single nucleotide is changed, resulting in a codon that codes for a different amino acid. Mutations that change an amino acid to a stop codon are called nonsense mutations.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, and/or any other molecular species with which contact is made in a reaction environment. Additional particularly relevant—but by no means limiting examples of molecular properties to be evolved include stabilities—e.g., the amount of a residual molecular property that is present after a specified exposure time to a specified environment, such as may be encountered during storage.

The term "mutating" refers to creating a mutation in a nucleic acid sequence; in the event where the mutation occurs within the coding region of a protein, it will lead to a codon change which may or may not lead to an amino acid change.

The term "mutations" means changes in the sequence of a wild-type nucleic acid sequence or changes in the sequence of a peptide or polypeptides. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

As used herein, the degenerate "N,N,N" nucleotide sequence represents 64 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular protein—as well as other synonymous terms— refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an protein" or "DNA encoding an protein" or "polynucleotide encoding a protein" and other synonymous terms encompasses a polynucleotide which includes only coding sequence for the protein as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants.

The term "population" as used herein means a collection of components such as polynucleotides, portions or polynucleotides or proteins. A "mixed population" means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g., glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modification (e.g. two proteolytic cleavages, or a proteolytic cleavage and a deglycosylation) can be distinguished en route to the production of a mature molecule, the reference precursor molecule may be termed a "pre-pro-form" molecule.

A "property" can describe any characteristic, including a physical, chemical, or activity characteristic property of a protein or antibody to be optimized. For example, in certain aspects, the predetermined property, characteristic or activity to be optimized can be selected from is selected from reduction of protein-protein aggregation, enhancement of protein stability, increased protein solubility, increased protein pH stability, increased protein temperature stability, increased protein solvent stability, increased selectivity, decreased selectivity, introduction of glycosylation sites, introduction of conjugation sites, reduction of immunogenicity, enhancement of protein expression, increase in antigen affinity, decrease in antigen affinity, change in binding affinity, change in immunogenicity, change in catalytic activity, pH optimization, or enhancement of specificity. An "optimized" property refers to a desirable change in a particular property in a mutant protein, antibody or cell compared to a template protein, antibody or cell, respectively.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" proteins refer to proteins produced by recombinant DNA techniques, i.e., produced from cells transformed by an exogenous DNA construct encoding the desired enzyme. "Synthetic" proteins are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "saturation" refers to a technique of evolution wherein every possible change is made at each position of a template polynucleotide or template polypeptide; however the change at each position is not confirmed by testing, but merely assumed statistically wherein the majority of possible changes or nearly every possible change is estimated to occur at each position of a template.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

The term "silent mutation" refers to a codon change that does not result in an amino acid change in an expressed polypeptide and is based on redundancy of codon usage for amino acid insertion.

As known in the art "similarity" between two enzymes is determined by comparing the amino acid sequence and its conserved amino acid substitutes of one protein to the sequence of a second protein. Similarity may be determined by procedures which are well-known in the art, for example, a BLAST program (Basic Local Alignment Search Tool at the National Center for Biological Information).

As used herein, the term "single-chain antibody" refers to a polypeptide comprising a VH domain and a VL domain in polypeptide linkage, generally liked via a spacer peptide (e.g., SEQ ID NO:1, and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al., 1989, which is hereby incorporated by reference in its entirety.

Also included in the invention are polypeptides having sequences that are "substantially identical" to the sequence of a polypeptide, such as one of any SEQ ID NO disclosed herein. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, "template oligopeptide" means a protein for which a secondary library of variants is desired. As will be appreciated by those in the art, any number of templates find use in the present invention. Specifically included within the definition of "proteins" or "oligopeptides" are fragments and domains of known proteins, including functional domains such as enzymatic domains, binding domains, etc., and smaller fragments, such as turns, loops, etc. That is, portions of proteins may be used as well. In addition, "protein" as used herein includes proteins, oligopeptides and peptides. In addition, protein variants, i.e., non-naturally occurring protein analog structures, may be used.

Suitable proteins include, but are not limited to, industrial and pharmaceutical proteins, including ligands, cell surface receptors, antigens, antibodies, cytokines, hormones, transcription factors, signaling modules, cytoskeletal proteins and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes are listed in the Swiss-Prot enzyme database. Suitable protein backbones include, but are not limited to, all of those found in the protein data base compiled and serviced by the Research Collaboratory for Structural Bioinformatics (RCSB, formerly the Brookhaven National Lab).

As used herein, the term "variable segment" refers to a portion of a nascent peptide which comprises a random, pseudorandom, or defined kernel sequence. A "variable segment" refers to a portion of a nascent peptide which comprises a random pseudorandom, or defined kernel sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "wild-type", or "wild type", means that the polynucleotide does not comprise any mutations. A "wild type" protein means that the protein will be active at a level of activity found in nature and will comprise the amino acid sequence found in nature.

DETAILED DESCRIPTION OF THE INVENTION

The disclosure provides a method of integrating therapeutic protein (including antibodies) generation and/or selection, evolution and expression in a mammalian host for manufacturing in a single system. In one embodiment of the CIAO method, therapeutic proteins, including antibodies, are generated, optimized and manufactured in the same mammalian host system. In another embodiment, protein therapeutics are discovered and manufactured in the same host. This optimizes manufacturing from the very beginning, saving costs (time and resources).

Historically, discovery of antibodies has been performed in eukaryotic (euk) and prokaryotic (prok) hosts. Typically, in bacteria (*E. coli*), partial length antibodies are discovered; for example, in phage display technologies, Fabs are recovered and sometimes converted to full length downstream. There are several potential disadvantages to these approaches.

In one example, there is some evidence that Fc and Fv regions communicate to effect antibody properties, such as binding and expression. Therefore, when an antibody fragment is optimized for a property such as expression, the improvement does not always translate to improved expression in the full length assembled antibody. For example, a library of Fc's was created in attempts to find a "holy grail" Fc that could be attached to any Fv to improve expression in any host.

In one aspect, codon mutagenesis was performed in the Constant Region for optimization of mammalian cell expression. Specifically 326 mutants were created in the constant region and expressed in HEK 293 and CHO-S cells. Screening was performed by ELISA. Several Fc's met the criteria of improved expression, and certain optimized Fc's were even identified that transferred positive effects across multiple cell lines; however, when a different Fv was attached to the Fc, the improvement in expression did not translate. This demonstrates that Fc's and Fv's communicate.

In order to avoid unexpected results upon recombination of antibody fragments, in one preferred aspect, the CIAO method is used to discover full length antibody molecules. In another preferred aspect, the CIAO method utilizes euk hosts.

In one embodiment, the eukaryotic system is a mammalian system is selected from one of the group consisting of CHO, HEK293, IM9, DS-1, THP-1, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC. In one aspect, the mammalian system is selected from a CHO or HEK293 cell line. In one specific aspect, the mammalian system is a CHO-S cell line. In another specific aspect, the mammalian system is a HEK293 cell line. In another embodiment, the eukaryotic system is a yeast cell system. In one aspect, the eukaryotic system is selected from *S. cerevisiae* yeast cells or *picchia* yeast cells.

In another embodiment, mammalian cell line creation can be performed commercially by a contract research or custom manufacturing organization. For example, for recombinant antibodies or other proteins, Lonza (Lonza Group Ltd, Basel, Switzerland) can create vectors to express product using the GS Gene Expression System™ technology with either CHOK1SV or NSO host cell lines.

In another embodiment, evolution can be performed in prok hosts (such as *E. coli*) and screens can occur in euk hosts (for example, CHO), as long as screening occurs in same host as manufacturing host.

Selection of Lead Candidate Protein(s)

A variety of methods can be used to discover, generate and/or select one or more therapeutic protein candidates to be evolved. Molecules selected can be existing recombinant proteins, or can come from collections of recombinant proteins, including enzymes, hormones and antibodies. Therapeutic proteins can include cloned human enzymes and hormones. Recombinant antibodies can be discovered using any number of generation and screening platforms available. Antibodies can be in any form, including single chain, fully human, Fab, Fv, Fc, bi-functional, chimeric, humanized, or fully human antibodies or fragments thereof. In one preferred aspect, the CIAO method is used to discover full length antibody molecules. Libraries of recombinant antibodies can be generated and screened using selection or screening systems in optimized or non-optimized mammalian hosts to yield candidates for evolution. Several eukaryotic expression systems are published, for example, mammalian or yeast cell systems.

In the method of the present invention, such mammalian expression systems, in particular systems using cell surface display of molecules for screening and selection, are employed to identify and select candidates for manufacturing, or evolution followed by manufacturing. Preferably, such mammalian hosts are Fibroblast cells (3T3, mouse; BHK21, Syrian hamster) Epithelial cells (MDCK, dog; Hela, human; PtK1, rat kangaroo) Plasma cells ((SP2/0 and NS0, mouse) Kidney cells (293, human; COS, monkey) Ovary cells (CHO, Chinese hamster) Embryonic cells (R1 and E14.1, mouse; H1 and H9, human; PER C.6, human). Cell surface display technology is employed to display proteins on the surface of the mammalian cells for screening. Proteins are cloned as fusions with membrane molecules which when expressed display the proteins on the surface of the cells for rapid, high-throughput screening, for example.

In certain embodiments, the disclosure provides a method of providing an optimized antibody. In one embodiment, an antigen is selected and a human antibody library is generated and expressed in a mammalian system, for example, CHO-S cells. The library is screened to identify fully human antibody hits, for example, by fluorescence activated cell sorting (FACS). The fully human antibody hits are then further screened/characterized by any relevant assay for at least one predetermined property, characteristic or activity. In one aspect, evolved molecules are screened for multiple characteristics simultaneously, for example, improved function and expression. The relevant assay can comprise for example, ELISA, or an array technology. A template antibody is selected from the human antibody hits. Any method of evolution is performed on the template antibody, or a fragment polypeptide thereof, to prepare a set of mutant antibodies. In one aspect, the evolution is performed by a method of comprehensive protein engineering to produce the set of mutant antibodies. The method of comprehensive protein engineering can be selected, for example, from one or a combination of Comprehensive Positional Evolution (CPE™), Comprehensive Protein Synthesis (CPS™), Flex Evolution, Synergy Evolution, Comprehensive Positional Insertion evolution (CPI™), or Comprehensive Positional Deletion evolution (CPD™). In another aspect, the mutant antibodies are expressed in the same mammalian system used to generate the human antibody library.

The set of mutant antibodies are characterized/screened for at least one predetermined property, characteristic or activity. In one aspect, the set of mutant antibodies is screened simultaneously, for example, for improved function and expression. In one aspect, a molecule specific database in the form of a functional positional map (an EvoMap™) is used for additional optimization by one or more protein evolution techniques known in the art; followed by identification and characterization of up-mutants. An optimized antibody is selected by comparison to the template antibody with respect to the at least one predetermined property, characteristic or activity.

In one aspect, gram scale expression of the selected optimized antibody is performed; followed by non-GLP toxicology. Stable cell line transfection, process development and generation of a Master Cell Bank is performed. GMP manufacturing is performed in the same mammalian system used to generate the human antibody library, for example, CHO-S cells, to result in an optimized therapeutic recombinant mABs.

In another embodiment, the CIAO method starts from selection of a template hybridoma or recombinant antibody; evolution of the antibody to provide a set of mutant antibodies which are screened by use of antibody cell surface display in a mammalian cell system; and manufacturing is performed in the same mammalian cell system used for screening.

In another embodiment, the selected template hybridoma/recombinant antibody is humanized and screened in the manufacturing host, followed by production in the manufacturing host, wherein the step of optimization (evolution) is omitted altogether.

In other aspects of the present invention, downstream expression optimization in manufacturing hosts is performed by evolving the Fc region of the antibody, silent codons in the antibody, and/or the vector and/or host genes used in protein expression. In one aspect, an Fc library is generated by any evolutionary technique. In one specific aspect of expression optimization, CPE is performed on Fc domain of an antibody to create a library of Fc mutants which can be used to select an optimal partner for any Fv. Optimization is designed for rapid attachment of all Fc CPE variants to each new Fv region. Alternatively, a subset of these Fcs can be used to attach to different Fvs. Each of these Fc CPE variant/Fv combinations is screened as a full-length antibody expressed in mammalian cells (e.g. CHO, cost-effective media) for optimal expression. Further, CPS can be performed to screen all theoretical permutations of up to 12 or more of these CPE hits in mammalian cells for expression improvement. Specific desirable codon changes can also be selected to identify clones with increased expression. Silent codons are identified and CPE is performed on these positions. This CPE library is screened to identify optimal expression hits. Further, all theoretical permutations of up to 12 or more CPE hits can be used in the CPS process to generate a new library that can be screened in mammalian cells for expression improvement. The top CPS silent mutation hits are used to customize protein for optimal expression in a specific cell line and media. This provides opportunity for biosimilar fine structure control.

Other areas for enhancement of expression include: optimization of the vector, including promoter, splice sites, 5' and 3' termini, flanking sequences, reduction of gene deletion and rearrangement, improvement of host cell gene activities, optimization of host glycosylating enzymes, and chromosome wide host cell mutagenesis and selection. It has been demonstrated that 5' amino acid sequences are important for enhancement of expression.

Evolution of Lead Candidates

Any method of protein evolution can be employed for simultaneous evolution of protein performance and expression optimization. Optimization of protein performance can include improvement of various characteristics such as affinity, pharmacokinetic characteristics, tissue targeting, protein-protein aggregation, addressing high assay variability and modifying other in vivo characteristics.

Methods for evolving molecules, including selected candidates of the present invention, include stochastic and non-stochastic methods. Published methods include random and non-random mutagenesis approaches. Any of these approaches can be employed to evolve properties of the therapeutic proteins of the present invention toward a desired characteristic, such as better stability in different temperature or pH environments, or better expression in a host cell. Other potentially desirable properties, such as improved catalytic activity, improved protein stability in various conditions, improved selectivity and/or solubility, and improved expression results by improvement of characteristics such as reduced aggregation can be selected for in evolution experiments.

Evolution is performed directly in a eukaryotic host, such as a mammalian cell host or a yeast cell host, that will be used for downstream production of the therapeutic protein. Candidates can be evolved for optimal expression in the same host used to screen and/or evolve and to manufacture. Expression optimization can be achieved by optimization of vectors used (vector components, such as promoters, splice sites, 5' and 3' termini and flanking sequences), gene modification of host cells to reduce gene deletions and rearrangements, evolution of host cell gene activities by in vivo or in vitro methods of evolving relevant genes, optimization of host glycosylating enzymes by evolution of relevant genes, and/or by chromosome wide host cell mutagenesis and selection strategies to select for cells with enhanced expression capabilities. Host cells are further described herein.

Cell surface display expression and screening technology (for example, as defined above) can be employed to screen libraries of evolved proteins for candidates to be manufactured.

Current methods in widespread use for creating alternative proteins from a starting molecule are oligonucleotide-directed mutagenesis technologies, error-prone polymerase chain reactions and cassette mutagenesis, in which the specific region to be optimized is replaced with a synthetically mutagenized oligonucleotide. In these cases, a number of mutant sites are generated around certain sites in the original sequence.

In oligonucleotide-directed mutagenesis, a short sequence is replaced with a synthetically mutagenized oligonucleotide. Error-prone PCR uses low-fidelity polymerization conditions to introduce a low level of point mutations randomly over a long sequence. In a mixture of fragments of unknown sequence, error-prone PCR can be used to mutagenize the mixture. In cassette mutagenesis, a sequence block of a single template is typically replaced by a (partially) randomized sequence.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations. U.S. Pat. No. 7,033,781 entitled "Whole cell engineering my mutagenizing a substantial portion of a starting genome, combining mutations, and optionally repeating" describes a method of evolving an organism toward desired characteristics. U.S. Pat. No. 6,764,835 entitled "Saturation mutagenesis in directed evolution" and U.S. Pat. No. 6,562,594 entitled "Synthetic ligation reassembly in directed evolution" describe methods of exhaustively evolving and screening for desired characteristics of molecules. Any such methods can be used in the method of the present invention.

There is a difference between previously known methods of "saturation mutagenesis" and techniques of "comprehensive" evolution preferred herein. Saturation mutagenesis refers to a technique of evolution wherein every possible change is made at each position of a template polynucleotide or template polypeptide; however the change at each position is not confirmed by testing, but merely assumed statistically. Comprehensive evolution refers to a technique of evolution wherein every possible change is made at each position of a template polynucleotide or template polypeptide and the polynucleotide or polypeptide is tested to confirm the intended change has been made.

Saturation methods are inherently statistical, non-comprehensive methods and were also never truly comprehensive across all the steps (for example, across mutant generation, mutant identification, mutant protein expression, mutant protein screening, and recombined up-mutant generation, identification, expression and screening). In comprehensive evolution techniques, each molecule is screened and confirmed at both the first step of mutagenesis, and further at a second step of recombining the up-mutants or hits.

Unless the saturation mutagenesis is confirmed by sequencing or some other method, the technique cannot be considered to be comprehensive for several possible reasons. For example, 1) cloning systems are not 100% efficient due to due to cloning or synthesis errors, or difficult to clone molecules or 2) some proteins are toxic when expressed and thus cannot be efficiently expressed. Therefore, it is important to confirm by sequencing, or some other technique, at each step. It is useful to score every step in order to screen for expression, so non-expressing clones don't get designated as "negative" as in previous work, they just get scored non-expressible. Comprehensive techniques are therefore considered to be more pure non-stochastic system than saturation techniques, as confirmed by the "confirmation" step.

Comprehensive Positional Evolution

Referring to FIG. 1, using a linear peptide as a simple example, in a first step, a set of naturally occurring amino acid variants (or a subset thereof, or amino acid derivatives) for each codon from position 1 to n (n corresponding to the number of residues in the polypeptide chain) is generated by a process referred to herein as Comprehensive Positional Evolution (CPE™). This procedure is repeated for each polypeptide chain of the target molecule. A minimum set of amino acid mutations contains only one codon for each of the 19 natural amino acids. However, it is recognized that each expression system may suffer from codon bias, in which insufficient tRNA pools can lead to translation stalling, premature translation termination, translation frame-shifting and amino acid misincorporation. Therefore, for expression optimization each set contains up to 63 different codons, including stop codons. In the next step, the mutations are confirmed by sequencing each new molecule. Other methods of confirmation can also be employed.

Each amino acid set is then screened for at least one of:
Improved function
Neutral mutations
Inhibitory mutations
Expression
Compatibility of the clone with the host system.

Preferably, multiple characteristics are screened for simultaneously such as, for example, improved function and expression.

The data for each set are combined for the entire polypeptide chain(s) and a detailed functional map (referred to herein as an EvoMap™) of the target molecule is generated. This map contains detailed information how each mutation affects the performance/expression and/or cloning capability of the target molecule. It allows for the identification of all sites where no changes can be made without a loss in protein function (e.g., antigen/receptor binding in case of antibodies). It also shows where changes can be made without affecting function. It further identifies changes that result in molecules that do not express in the host system, and therefore do not assess the effect of the mutation.

A schematic of a hypothetical EvoMap™ is shown in FIG. 1. Each position on the template is identified as a restricted site (non-mutable), a fully mutable site, a partially mutable site or an up-mutant for a specific amino acid substitution. Each partially mutable site may be further designated as amenable to substitution with, for example, a charged residue, or a non-polar residue substitution, and a non-expressing clone and/or molecule that cannot be cloned in the host system.

It is possible to utilize the EvoMap™ in order to recognize and recombine beneficial single amino acid substitutions, and screen to further optimize the desired characteristics in the target molecule. However, evolution of certain characteristics may require two or more simultaneous mutations to become observable. The EvoMap™ may be exploited to efficiently, and cost effectively, produce a set of multi-site mutant polypeptides in a non-random fashion. The set of multi-site mutant polypeptides can then be screened for multi-site upmutants.

CPE enables the complete in vivo confirmed protein mutation map. Identification of the entire set of up-mutants enables further combinatorial evolution step(s). CPE can be utilized in order to reduce the immunogenicity risk of evolved proteins by the selection of non-surface mutations; elimination of T-cell epitopes; and mimicry of somatic mutations.

In one aspect, CPE can be used to generate a library of up to 5, 10 or 15 amino acids, or up to all 19 amino acids. Changes are made at each position in the protein and screened for a desirable characteristic, such as binding affinity or expression, and the Evomap™ is created. Later rounds of mutation and screening can be used to generate the data for all 19 amino acids. From the map, fully mutable sites are identified. These sites are useful to identify positions that can be modified to create a new collection of molecules that can be made and tested for new characteristics. For example, informatics can be employed to identify HLA haplotypes in the sequence, and desired changes can be made to avoid these haplotypes by making specific targeted changes at "neutral" ("fully mutable") sites identified from the map, where the primary characteristic will not be affected. This could potentially reduce immunogenicity risk (one could select non-surface mutations, eliminate t-cell epitopes, mimic hypersomatic mutations). Further, the map can show sites for site specific modifications (glycosylation and chemical conjugation) to improve various characteristics. Also, optimization of silent mutations can improve protein expression in a variety of hosts.

Synergy Evolution

Figure 2:
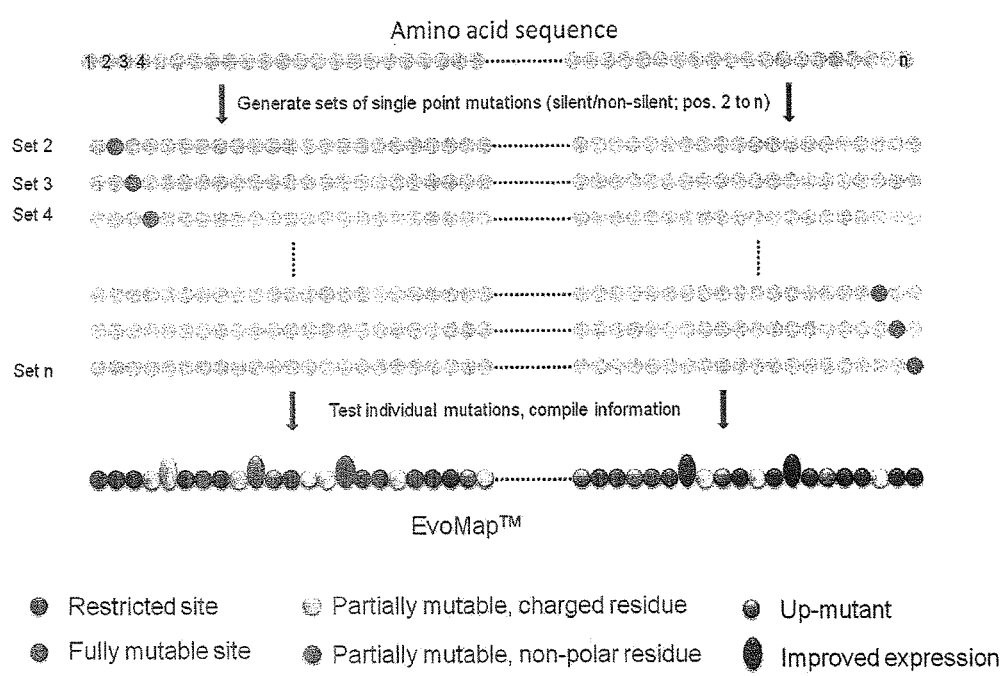
FIG. 2 illustrates how comprehensive positional evolution (CPE™) is used to generate a molecule specific database (EvoMap™).

In one embodiment of the present invention, an EvoMap™ is generated and utilized for Synergy Evolution, as shown in FIG. 2. In Synergy Evolution, simultaneous mutation at 2-20 selected sites may be combined to produce a combinatorial effect. The EvoMap™ of the template polypeptide is used to select specific single amino acid point mutations for assembly to multi-site polypeptide mutations.

In Synergy Evolution, non-deactivating amino acid point mutations are selected from within partially mutable sites that are near non-mutable sites on the EvoMap™. In one aspect, the selected non-deactivating point mutations are adjacent to non-mutable sites. In Synergy Evolution, simultaneous mutation of amino acids at two to 20 of the selected sites is performed for combinatorial effects. In one aspect, recombination of two to 20 selected mutations is used to produce a codon variant library coding for a population of multi-site mutant polypeptides. Following cloning and expression, the multi-site mutant polypeptides produced are then screened for at least one predetermined property, characteristic or activity compared to the template polypeptide. In this manner, multi-site upmutant polypeptides can be identified. In one aspect, multi-site mutant polypeptides are produced by combinatorial protein synthesis. One advantage of Synergy Evolution is that it does not require a protein x-ray crystal structure to direct evolution of the template polypeptide. This technique is useful particularly for proteins with high assay variation and other multi-site effects.

According to the present invention, applications of Synergy Evolution include, but are not limited to evolution of complex molecular mechanistic changes, evolution of proteins with high assay variation, evolution of protein specificity, improvement of expression in various expression hosts, improvement of protein catalytic activity, stability, and pH optimization. Synergy Evolution is applicable to all protein therapeutic types including, but not limited to, hormones, enzymes, cytokines and antibodies.

In one aspect of the present invention, Synergy Evolution can be used to optimize one or more aspects of a polypeptide which is a portion of a protein molecule. The protein molecule can be assembled by ligating one or more mutant nucleic acids coding for polypeptides with zero, one or more nucleic acids coding for framework polypeptides to create a variant protein by cloning, translation and expression techniques known in the art. In one aspect, a framework polypeptide is derived from a wild-type protein molecule. In this aspect, Synergy Evolution can be used in conjunction with antibody humanization techniques. For example, a mouse monoclonal antibody may be selected for evolution and humanization. The CDR regions of the antibody are cloned and sequenced and individual CDR regions (CDR1, CDR2, CDR3) may be synthesized and ligated to other nucleotides coding for human antibody framework polypeptides, followed by production of a human variant IgG library. The human variant IgG library is then screened for at least one property, for example two or more properties including improved function and expression, compared to the mouse mAb. In another aspect, a framework polypeptide is an artificial scaffold polypeptide. Specific techniques of ds DNA fragment preparation, ligation and assembly of nucleic acids, cloning, transfection, expression, solid phase synthesis of libraries, solution phase synthesis of libraries, comprehensive positional evolution, combinatorial protein synthesis, quantification of expression by ELISA quantification and β-galactosidase assay, and functional ELISA are presented in the examples section.

In another embodiment of the invention, Synergy Evolution can be used to enhance binding affinity of an antibody. In this embodiment, optimization of the antibody variable region may be performed. For example, for the production of antibody mutants, CPE is performed for light chain and heavy chain variable regions of a selected antibody and an EvoMap™ is generated. Mutants are selected for reassembly; for example, variants of the light chain are selected and variants of the heavy chain are selected for assembly. Non-deactivating amino acid point mutations are selected from within partially mutable sites that are near non-mutable sites. The reassembly technology utilizing CPS can be used to create a library of heavy chains. The light chain variants can be combined with the heavy chain variants, cloned, expressed and the variants are screened as full IgGs from eukaryotic cell line supernatants. Binding affinity for certain variants is assessed by, for example, use of ELISA, BIAcore and/or Sapidyne instrumentation assays, or other techniques known to one in the art.

Flex Evolution

In another embodiment, the CPE/EvoMap may be used to identify and exploit fully mutable sites. In one aspect, exploitation of multiple fully mutable sites is termed Flex Evolution and is used to make targeted changes such as introduction of sites for glycosylation (e.g. codons for amino acids for N- or O-linked glycosylation; Asn within consensus sequence Asn-Aa-Ser-Thr or Ser/Thr) and chemical conjugation. Flex evolution may also be used in design of protease cleavage sites, introduction of tags for purification and/or detection, site-specific labeling, and the like. Further, codon optimization of silent mutations may be utilized for improvement of protein expression. In this embodiment, termed Flex Evolution, following protein expression, the mutant polypeptide libraries produced are rescreened for at least one predetermined property, characteristic or activity compared to the template polypeptide. In one aspect, the predetermined property includes reduction of protein-protein aggregation, enhancement of protein stability, or increased protein solubility. In one aspect, the mutant polypeptide libraries are screened for two or more properties simultaneously. In another aspect, any eukaryotic expression system which glycosylates may be used for the introduction of glycosylation sites, such as, for example, mammalian, plant, yeast, and insect cell lines.

In Flex Evolution, evaluation of bioinformatics and protein x-ray crystal structures of related proteins, or the template protein or polypeptide, is useful for template optimization. In one aspect, selected sites are not at contact residues. In another aspect, selection of non-surface protein mutations allows for reduced immunogenicity risk.

Applications of Flex Evolution include, bit are not limited to, reduction of protein-protein aggregation, improvement of protein solubility, optimization of pharmacokinetics via glycosylation libraries, optimization of protein secondary and tertiary structure and deimmunization of antigenic sites directly via either mutation sets or indirectly through glycosylation masking.

In one aspect of Flex Evolution, an EvoMap™ is utilized to identify fully mutable sites, CPS generation is performed with insertion of glycosylating residues to fully mutable sites (or silent mutations for translation effects), and screening of combinatorial glycosylated library is performed by analytical analysis (e.g. Mass Spectroscopy analysis, Dynamic Light Scattering), immunogenicity reduction (by bioinformatics or assay), and/or pharmacokinetic analysis (e.g. in Foxn1nu mice).

In one aspect, Flex evolution may be used for deimmunization to eliminate immunogenicity while maintaining function. Flex Evolution deimmunization can be performed by masking immunogenicity with glycosylation, identifying human hypersomatic mutation spectra amino acid substitutions that may eliminate immunogenicity while maintaining function, reduction of dose for evading immunogenicity potential, and minimization of non-surface amino acid residue changes. Further, immunogenicity databases and algorithms can be used to identify and replace potential MHC binding epitopes. In one aspect, in silico modification prediction is coupled with CPE/CPS data to generate variants.

Reduced propensity to generate T-cell epitopes and/or deimmunization may be measured by techniques known in the art. Preferably, deimmunization of proteins may be tested in vitro by T cell proliferation assay. In this assay PBMCs from donors representing >80% of HLA-DR alleles in the world are screened for proliferation in response to either wild type or deimmunized peptides. Ideally cell proliferation is only detected upon loading of the antigen-presenting cells with wild type peptides. Additional assays for deimmunization include human in vitro PBMC re-stimulation assays (e.g. interferon gamma (TH1) or IL4 (TH2) ELISA. Alternatively, one may test deimmunization by expressing HLA-DR tetramers representing all haplotypes. In order to test if de-immunized peptides are presented on HLA-DR haplotypes, binding of e.g. fluorescence-labeled peptides on PBMCs can be measured. Measurement of HLA Class I and Class II transgenic mice for responses to target antigen (e.g. interferon gamma or IL4). Alternatively epitope library screening with educated T cells (MHCI 9mer; MHCII 20mer) from PBMC and/or transgenic mouse assays. Furthermore, deimmunization can be proven by determining whether antibodies against the deimmunized molecules have been generated after administration in patients.

In another embodiment, the Flex Evolution techniques of the present invention can be utilized for expression optimization. In one aspect, the present invention discloses the utilization of protein engineering methods to develop silent mutation codon optimized Fc variants with improved expression in eukaryotic cells. A silent mutation is one in which the variation of the DNA sequence does not result in a change in the amino acid sequence of the protein. In one aspect, codon mutagenesis is performed in the constant region for optimization of eukaryotic cell expression. A codon optimized Fc variant with improved expression properties while retaining the capacity to mediate effector functions improves the production of therapeutic antibodies. In this aspect, for example, a constant region of an antibody molecule can be evolved for screening in different expression hosts, for example, mammalian cell lines expression screening utilizing CHO, HEK293 and COS-7. One example of expression optimization by codon mutagenesis in the constant region for mammalian cell expression is shown in FIG. 3 and described in Example 19. The expression levels shown are each an average of 4 data points, and confirmed over multiple experiments. Multiple cell line capability was demonstrated for first mutant tested in HEK293 and CHO cell line expression systems.

In addition, the EvoMap™ may be used to generate 3-dimensional computational molecular models of the oligopeptide, or specific regions thereof, to explore the structural mechanisms involved in, e.g., antibody-epitope specificity and stability. A hypothetical three-dimensional EvoMap™ is shown in FIG. 13.

The information in EvoMap can also be combined with structural information (if available) to select e.g., only surface residues for mutations to increase solubility/decrease aggregation.

Comprehensive Positional Insertion Evolution

In one embodiment, the disclosure provides methods of identifying and mapping mutant polypeptides formed from, or based upon, a template polypeptide. Referring to FIG. 8, using a linear peptide as a simple example, in a first step, a set of naturally occurring amino acid variants (or a subset thereof, or amino acid derivatives) for each codon from position 2 to n (n corresponding to the number of residues in the polypeptide chain) is generated by a process referred to herein as Comprehensive Positional Insertion (CPI™) evolution.

In CPI™, an amino acid is inserted after each amino acid throughout a template polypeptide one at a time to generate a set of lengthened polypeptides. CPI can be used to insert 1, 2, 3, 4, or up to 5 new sites at a time. Each of the 20 amino acids is added at each new position, one at a time, creating a set of 20 different molecules at each new position added in the template. In this case, position 1, which is methionine and invariant, is skipped. This procedure is repeated for each polypeptide chain of the target molecule. A minimum set of amino acid mutations contains only one codon for each of the 20 natural amino acids.

The present invention relates to methods of identifying and mapping mutant polypeptides formed from, or based upon, a template polypeptide. Typically, the polypeptide will comprise n amino acid residues, wherein the method comprises (a) generating $n+[20\times(n-1)]$ separate polypeptides, wherein each polypeptide differs from the template polypeptide in that it has inserted after each position in the template each of the 20 amino acids one at a time (as illustrated in FIG. 1); assaying each polypeptide for at least one predetermined property, characteristic or activity; and (b) for each member identifying any change in said property, characteristic or activity relative to the template polypeptide.

In one embodiment, one or more regions are selected for mutagenesis to add one position at a time as described above. In such case, n represents a subset or region of the template polypeptide. For example, where the polypeptide is an antibody, the entire antibody or one or more complementarity determining regions (CDRs) of the antibody are subjected to mutagenesis to add one position at a time in the template polypeptide after each position.

The invention thus includes methods of mapping a set of mutant antibodies formed from a template antibody having at least one, and preferably six, complementarity determining regions (CDRs), the CDRs together comprising n amino acid residues, the method comprising (a) generating $n+[20\times(n-1)]$ separate antibodies, wherein each antibody differs from the template antibody in that has inserted a single predetermined position, one at a time, after each position in the template sequence; (b) assaying each set for at least one predetermined property, characteristic or activity; and (c) for each member identifying any change in a property, characteristic or activity relative to the template polypeptide. For antibodies, the predetermined property, characteristic or property may be binding affinity and/or immunogenicity, for example.

In addition, provided are methods of producing a set of mutant antibodies formed from a template antibody having at least one complementarity determining region (CDR), the CDR comprising n amino acid residues, the method comprising: (a) generating n+[20×(n−1)] separate antibodies, wherein each antibody differs from the template antibody in that it has an extra amino acid added at a single predetermined position of the CDR. In another embodiment, the antibody comprises six CDRs, and together the CDRs comprise n amino acid residues.

In another embodiment, the new lengthened polypeptides described above are further mutated and mapped after screening to identify a change in a property, characteristic or activity relative to the shortened polypeptide. Typically, the lengthened polypeptide will comprise n amino acid residues, wherein the method comprises (a) generating n (n−1 in the case where the initial residue is methionine) separate sets of polypeptides, each set comprising member polypeptides having X number of different predetermined amino acid residues at a single predetermined position of the polypeptide; wherein each set of polypeptides differs in the single predetermined position; assaying each set for at least one predetermined property, characteristic or activity; (b) for each member identifying any change in said property, characteristic or activity relative to the template polypeptide; and optionally (c) creating a functional map reflecting such changes. Preferably, the number of different member polypeptides generated is equivalent to n×X (or [n−1]×X, as the case may be).

In the alternative, the method comprises generating a single population comprising the sets of mutated polypeptides from the lengthened polypeptides. In this embodiment, the entire new population is screened, the individual members identified, and the functional map generated.

Typically, where each naturally occurring amino acid is used, X will be 19 (representing the 20 naturally occurring amino acid residues and excluding the particular residue present in a given position of the template polypeptide). However, any subset of amino acids may be used throughout, and each set of polypeptides may be substituted with all or a subset of the total X used for the entire population.

However, it is recognized that each expression system may suffer from codon bias, in which insufficient tRNA pools can lead to translation stalling, premature translation termination, translation frameshifting and amino acid misincorporation. Therefore, for expression optimization each set contains up to 63 different codons.

Each amino acid set is then screened for at least one, and preferably two or more, desirable characteristic such as improved function; neutral mutations, inhibitory mutations, and expression.

In one aspect, the lengthened polypeptides can be mapped to identify a change in a property, characteristic or activity resulting in the shortened polypeptides relative to the "wild-type". The data for each set are combined for the entire polypeptide, or "target molecule". Hits from the screening of the lengthened polypeptides (target molecules) can then be used for further comprehensive mutagenesis chain(s) and screening as described herein. The data from mutagenesis provides a detailed functional map (referred to herein as an EvoMap™) of the target molecule is generated. This map contains detailed information how each mutation affects the performance/expression of the target molecule. It allows for the identification of all sites where no changes can be made without a loss in protein function (or antigen/receptor binding in case of antibodies). It also shows where changes can be made without affecting function.

In another aspect, CPE can be used to generate a library of 5, 10, up to 15, or up to all 19 amino acids at each position of interest.

Comprehensive Positional Deletion Evolution

Comprehensive Positional Deletion Evolution (CPD™) relates to methods of identifying and mapping mutant polypeptides formed from, or based upon, a template polypeptide. CPD evolution deletes every amino acid through the protein one position at a time. Typically, the polypeptide will comprise n amino acid residues, wherein the method comprises (a) generating n−1 (n−2 in the case where the initial residue is methionine) separate polypeptides, wherein each polypeptide differs from the template polypeptide in that it lacks a single predetermined position; assaying each polypeptide for at least one predetermined property, characteristic or activity; and (b) for each member identifying any change in said property, characteristic or activity relative to the template polypeptide.

In one embodiment of CPD evolution, one or more regions are selected for mutagenesis to remove one position at a time. In such case, n represents a subset or region of the template polypeptide. For example, where the polypeptide is an antibody, the entire antibody or one or more complementarity determining regions (CDRs) of the antibody are subjected to mutagenesis to remove one position at a time in the template polypeptide.

In one embodiment, CPD thus includes methods of mapping a set of mutant antibodies formed from a template antibody having at least one, and preferably six, complementarity determining regions (CDRs), the CDRs together comprising n amino acid residues, the method comprising (a) generating (n−1) separate antibodies, wherein each antibody differs from the template antibody in that lacks a single predetermined position; (b) assaying each set for at least one predetermined property, characteristic or activity; and (c) for each member identifying any change in a property, characteristic or activity relative to the template antibody. For antibodies, the predetermined property, characteristic or property may be binding affinity and/or immunogenicity, for example.

One aspect of CPD evolution includes methods of producing a set of mutant antibodies formed from a template antibody having at least one complementarity determining region (CDR), the CDR comprising n amino acid residues, the method comprising: (a) generating n−1 separate antibodies, wherein each antibody differs from the template antibody in that lacks a single predetermined position of the CDR. In another embodiment, the antibody comprises six CDRs, and together the CDRs comprise n amino acid residues.

In another embodiment of CPD evolution, the new shortened polypeptides described above are further mutated and mapped after screening to identify a change in a property, characteristic or activity relative to the shortened polypeptide. Typically, the shortened polypeptide will comprise n amino acid residues, wherein the method comprises (a) generating n (n−1 in the case where the initial residue is methionine) separate sets of polypeptides, each set comprising member polypeptides having X number of different predetermined amino acid residues at a single predetermined position of the polypeptide; wherein each set of polypeptides differs in the single predetermined position; assaying each set for at least one predetermined property, characteristic or activity; (b) for each member identifying any change in said property, characteristic or activity relative to the template polypeptide; and (c) creating a functional map reflecting such changes. Preferably, the number of different member polypeptides generated is equivalent to n×X (or [n−1]×X, as the case may be).

In the alternative, the CPD method comprises generating a single population comprising the sets of mutated polypeptides from the shortened polypeptides. In this embodiment, the entire new population is screened, the individual members identified, and the functional map generated. Typically, where each naturally occurring amino acid is used, X will be 19 (representing the 20 naturally occurring amino acid residues and excluding the particular residue present in a given position of the template polypeptide). However, any subset of amino acids may be used throughout, and each set of polypeptides may be substituted with all or a subset of the total X used for the entire population.

Any mutational or synthetic means may be used to generate the set of mutants in CPD evolution. In one embodiment, the generation of polypeptides comprises (i) subjecting a codon-containing polynucleotide encoding for the template polypeptide to polymerase-based amplification using a 64-fold degenerate oligonucleotide for each codon to be mutagenized, wherein each of the 64-fold degenerate oligonucleotides is comprised of a first homologous sequence and a degenerate N,N,N triplet sequence, so as to generate a set of progeny polynucleotides; and (ii) subjecting the set of progeny polynucleotides to clonal amplification such that polypeptides encoded by the progeny polynucleotides are expressed.

In one embodiment of CPD evolution, the entire shortened polypeptide is subjected to saturation mutagenesis. In another embodiment, one or more regions are selected for saturation mutagenesis. In such case, n represents a subset or region of the template polypeptide. For example, where the polypeptide is an antibody, the entire antibody or one or more complementarity determining regions (CDRs) of the antibody are subjected to saturation mutagenesis.

The CPD evolution disclosure thus includes methods of mapping a set of mutant antibodies formed from a shortened template antibody having at least one, and preferably six, complementarity determining regions (CDRs), the CDRs together comprising n amino acid residues, the method comprising (a) generating n separate sets of antibodies, each set comprising member antibodies having X number of different predetermined amino acid residues at a single predetermined position of the CDR; wherein each set of antibodies differs in the single predetermined position; and the number of different member antibodies generated is equivalent to n x X; (b) assaying each set for at least one predetermined property, characteristic or activity; (c) for each member identifying any change in a property, characteristic or activity relative to the template polypeptide; and (d) creating a structural positional map of such changes. For antibodies, the predetermined property, characteristic or property may be binding affinity and/or immunogenicity. As set forth above, in the alternative a single population comprising all sets of mutated antibodies may be generated.

In addition, provided are methods of producing a set of mutant antibodies formed from a shortened template antibody having at least one complementarity determining region (CDR), the CDR comprising n amino acid residues, the method comprising: (a) generating n separate sets of antibodies, each set comprising member antibodies having X number of different predetermined amino acid residues at a single predetermined position of the CDR; wherein each set of antibodies differs in the single predetermined position; and the number of different member antibodies generated is equivalent to n x X. In another embodiment, antibody comprises six CDRs, and together the CDRs comprise n amino acid residues.

The CPD™ evolution method includes a functional positional map (EvoMap™) made by the methods described herein. In an additional embodiment, certain residues particularly sensitive to change may be so indicated on the EvoMap™. Further optimization may be implemented by making additional mutational changes at positions outside of these sensitive positions. It is also possible to utilize the EvoMap™ in order to recognize and recombine beneficial single amino acid substitutions, and screen to further optimize the desired characteristics in the target molecule, in a process called Combinatorial Protein Synthesis (CPS™).

Combinatorial Protein Synthesis

Figure 3:
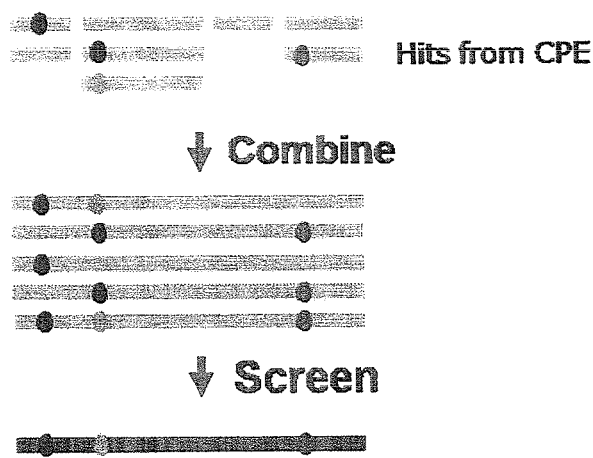
FIG. 3 shows a schematic of Comprehensive Positional Synthesis (CPS) which can be used to combine up-mutants from CPE™
Figure 4:
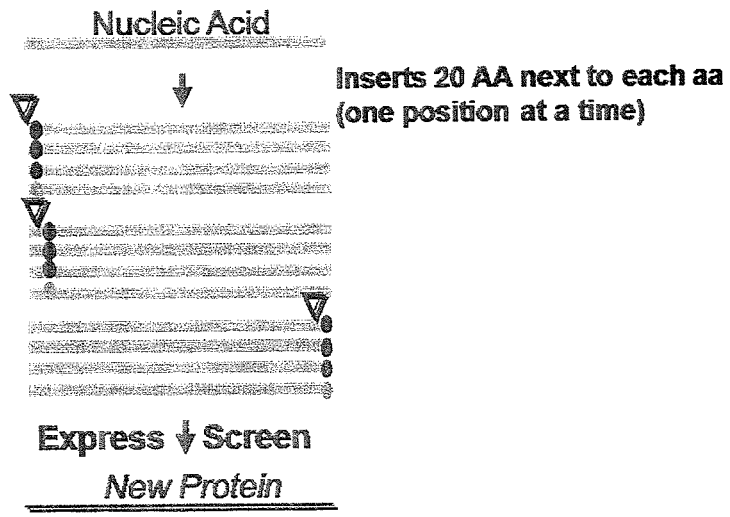
FIG. 4 shows a schematic of Comprehensive Positional Insertion (CPI™) evolution.
Figure 5:
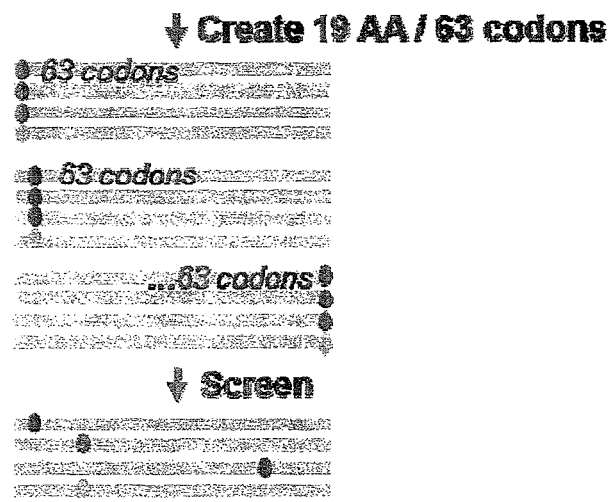
FIG. 5 illustrates one combination of evolution methods: a lengthened nucleic acid from CPI™ evolution is subjected to Comprehensive Positional Evolution (CPE™) and used to generate a molecule specific database (EvoMap™).
Figure 6:
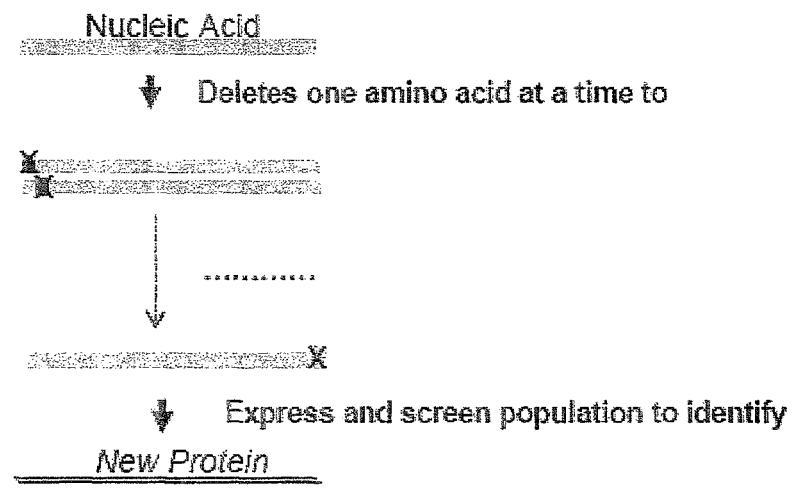
FIG. 6 shows a schematic of Comprehensive Positional Deletion (CPD™) evolution.
Figure 7:
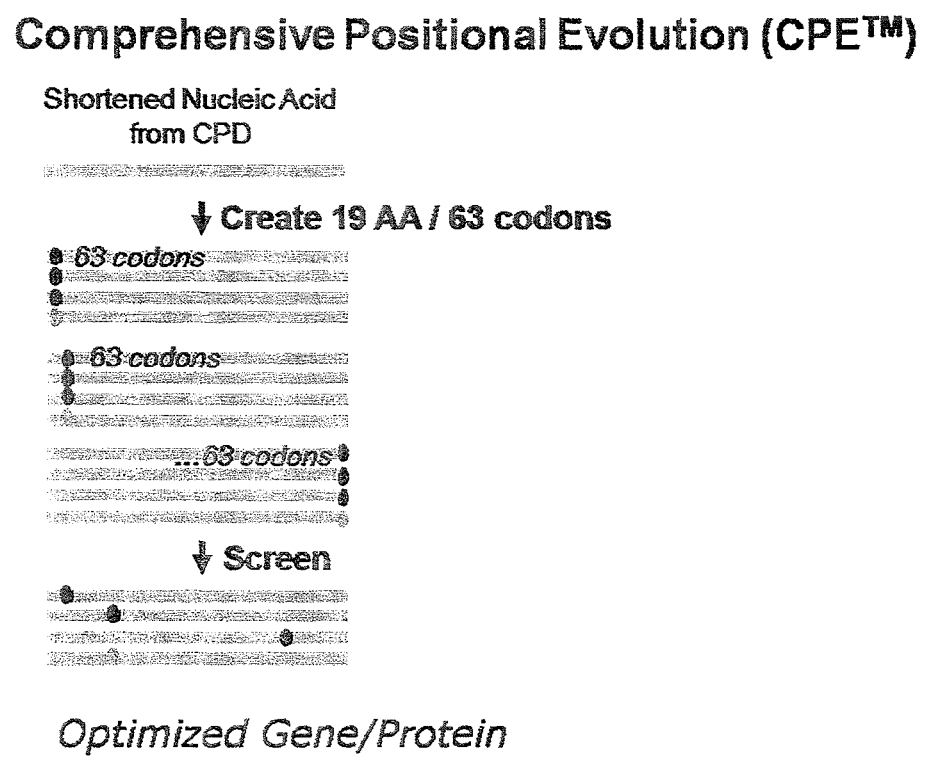
FIG. 7 illustrates another combination of evolution methods: a shortened nucleic acid from CPD™ evolution is subjected to Comprehensive Positional Evolution (CPE™) and used to generate a molecule specific database (EvoMap™).

Combinatorial Protein Synthesis (CPS™) involves combining individual hits from CPE, CPI, CPD, or any other evolutionary technique to combine two or more mutations. CPS is used to synthesize proteins with combined mutations which are then screened for optimized gene and protein characteristics. A schematic of CPS™ is shown in FIG. 3. In one aspect, two or more point mutations which result in up-mutants or neutral mutations are combined in CPS.

In one embodiment CPE is combined with CPS to create mutants, which are screened for the desired property. In one aspect, time and resources can be saved in the CPE process by changing 2 aa or 3 aa or 4 aas at a time versus one at a time; so if the number of aa's in the protein is N, the total number generated and screened for 2 aa at a time would be $(20^2) \times \frac{1}{2}N$; 3 at a time would be $(20^3) \times \frac{1}{3}N$, etc. For example, in one specific aspect, (in the 2aa example): $1^{st}$ aa at $1^{st}$ aa position is combined with all 20 at the $2^{nd}$ aa position and all the other aa's remain the same, then the $2^{nd}$ aa at $1^{st}$ aa position is combined with all 20 at the $2^{nd}$ aa position and all other aa's remain the same. The entire population is screened for up mutants and then mutation at the second set of the next two aa's down the line is performed. In a similar aspect, this can be performed for 3aas at a time or 4aas at a time. In another aspect, optionally follow the CPE process with CPS of upmutants (including any subset thereof).

In one aspect, non-natural amino acids can be incorporated into the process (so all 19 other amino acids, or a subset thereof, plus non-natural amino acids) by using novel technologies such as the quadruplet codon described in the attached and related papers. Neumann et al. Encoding multiple unnatural amino acids via evolution of a quadruplet-decoding ribosome *Nature* 464, 441-444 (14 Feb. 2010). In this aspect CPE/CPS is performed for incorporation of non-natural amino acids.

In a further aspect, the entire CPE library is created synthetically (synthesizing all the molecules on commercially available machines). In the event the synthesis machine cannot create large enough strands, fragments are synthesized and then ligated to generate full length molecules. This library is screened and followed with CPS to combine desired mutations. This is a two step process wherein CPE is followed by CPS, not one step of only CPE.

In another aspect, a CPE library is generated and screened, then followed by CPS combining up mutants as follows: if there are 10 up-mutants, test a single molecule with all 10 changes, then test all versions of 9 mutations, then 8, 7, 6, 5 etc. until one of the groups does not find an improved molecule over any in the previous group. Once an improved molecule is identified the process can be terminated.

In a further aspect, CPE is performed to identify up-mutants and neutral mutations for affinity and expression, then CPS is performed with combinations of up mutants and neutral mutations, and the library is rescreened for further improvements in characteristics such as function, affinity and/or expression.

In a further aspect, CPE is performed on codons of the Fc or other domain for glycosylation changes.

In another aspect, CPE or CPE combined with CPS of microRNA's or introns can be performed.

In a further aspect, CPE or CPE combined with CPS of rodent antibody CDRs is performed, then screened for up-mutants, followed by humanization.

In one aspect, CPE or CPE combined with CPS is performed to produce alternative intermediate nucleotides that lead to the desired mutation in the final reaction, for example, a methylated cytosine that converts to a uracil.

In one aspect, CPE or CPE combined with CPS plus informatics is utilized for converting mouse CDR's to human CDR's and vice versa.

In one aspect, CPE or CPE combined with CPS is utilized with 2 and 3 mutations spaced throughout the protein.

In another aspect, CPE or CPE combined with CPS are used in a dual chain vector for screening evaluation for increased sensitivity.

In a further aspect, CPE or CPE combined with CPS is utilized for selecting for allosteric changes.

Any of several screening techniques can be used to evaluate CPE/CPS mutants. In one aspect CPE or CPE combined with CPS mutants can be secreted and displayed in eukaryotic hosts. Alternatively, CPE or CPE combined with CPS mutants can be produced in *E. coli* and screened in eukaryotic hosts. In another aspect, CPE is performed starting at 15aa or 10aa and followed by CPS; then followed up with the rest of the remaining 19aa. In another aspect, CPE or CPE combined with CPS is utilized for evolving proteins specifically with non-surface amino acid changes. In one aspect, CPE for can be utilized for multi-dimensional epitope mapping. In another aspect, CPE or CPE combined with CPS screening can be performed transiently in eukaryotic cells. In a further aspect, CPE or CPE combined with CPS is performed, then sequencing and array of all clones is performed, for example, in a chip based or well-based format for expression and screening. In another aspect, CPE or CPE combined with CPS is utilized for evolving metal ion coordination by selecting in varying ion concentrations. In a further aspect, CPE or CPE combined with CPS is performed, and proteins are expressed and screened in cell free conditions and in non-human living organisms. In one aspect, CPE or CPE combined with CPS screening of stem cells is performed for varying effects on differentiation and protein and RNA and mRNA expression. In a further aspect, CPE or CPE combined with CPS multiplex screening is performed for multiple protein characteristics like expression and binding. In another aspect, CPE or CPE combined with CPS is performed on template molecules involved in brain transport and membrane crossing; and mutants are screened for improved characteristics. In one aspect, CPE or CPE combined with CPS mutants are screened for protein hygroscopic characteristics. In another aspect, CPE or CPE combined with CPS mutants are assayed for selecting dynamic proteins. In one aspect, CPE or CPE combined with CPS screening is performed outside of the target condition to identify mutants within target condition and vice versa.

In one embodiment, any of the above aspects of CPE or CPE combined with CPS are utilized in combination with a method selected from CPI, CPD, and CPD with CPI combination.

In another embodiment, any of the above aspects of CPE or CPE combined with CPS are utilized in combination with a method selected from Flex evolution and Synergy evolution performed from a template.

The term "template" may refer to a base polypeptide or a polynucleotide encoding such polypeptide. As would be appreciated by one of skill in this art, any template may be used in the methods and compositions of the present invention. Templates which can be mutated and thereby evolved can be used to guide the synthesis of another polypeptide or library of polypeptides as described in the present invention. As described in more detail herein, the evolvable template encodes the synthesis of a polypeptide and can be used later to decode the synthetic history of the polypeptide, to indirectly amplify the polypeptide, and/or to evolve (i.e., diversify, select, and amplify) the polypeptide. The evolvable template is, in certain embodiments, a nucleic acid. In certain embodiment of the present invention, the template is based on a nucleic acid. In other embodiments, the template is a polypeptide.

The nucleic acid templates used in the present invention are made of DNA, RNA, a hybrid of DNA and RNA, or a derivative of DNA and RNA, and may be single- or double-stranded. The sequence of the template is used to encode the synthesis of a polypeptide, preferably a compound that is not, or does not resemble, a nucleic acid or nucleic acid analog (e.g., an unnatural polymer or a small molecule). In the case of certain unnatural polymers, the nucleic acid template is used to align the monomer units in the sequence they will appear in the polymer and to bring them in close proximity with adjacent monomer units along the template so that they will react and become joined by a covalent bond. In certain other embodiments, the template can be utilized to generate non-natural polymers by PCR amplification of a synthetic DNA template library consisting of a random region of nucleotides.

It will be appreciated that the template can vary greatly in the number of bases. For example, in certain embodiments, the template may be 10 to 10,000 bases long, preferably between 10 and 1,000 bases long. The length of the template will of course depend on the length of the codons, complexity of the library, length of the unnatural polymer to be synthesized, complexity of the small molecule to be synthesized, use of space sequences, etc. The nucleic acid sequence may be prepared using any method known in the art to prepare nucleic acid sequences. These methods include both in vivo and in vitro methods including PCR, plasmid preparation, endonuclease digestion, solid phase synthesis, in vitro transcription, strand separation, etc. In certain embodiments, the nucleic acid template is synthesized using an automated DNA synthesizer.

As discussed above, in certain embodiments of the invention, the method is used to synthesize polypeptides that are not, or do not resemble, nucleic acids or nucleic acid analogs. Thus, in certain embodiments of the present invention, the nucleic acid template comprises sequences of bases that encode the synthesis of an unnatural polymer or small molecule. The message encoded in the nucleic acid template preferably begins with a specific codon that bring into place a chemically reactive site from which the polymerization can take place, or in the case of synthesizing a small molecule the "start" codon may encode for an anti-codon associated with a small molecule scaffold or a first reactant. The "start" codon of the present invention is analogous to the "start" codon, ATG, which encodes for the amino acid methionine.

In yet other embodiments of the invention, the nucleic acid template itself may be modified to include an initiation site for polymer synthesis (e.g., a nucleophile) or a small molecule scaffold. In certain embodiments, the nucleic acid template includes a hairpin loop on one of its ends terminating in a reactive group used to initiate polymerization of the monomer units. For example, a DNA template may comprise a hairpin loop terminating in a 5'-amino group, which may be protected or not. From the amino group polymerization of the unnatural polymer may commence. The reactive amino group can also be used to link a small molecule scaffold onto the nucleic acid template in order to synthesize a small molecule library.

To terminate the synthesis of the unnatural polymer a "stop" codon should be included in the nucleic acid template preferably at the end of the encoding sequence. The "stop" codon of the present invention is analogous to the "stop" codons (i.e., TAA, TAG, TGA) found in mRNA transcripts. These codons lead to the termination of protein synthesis. In certain embodiments, a "stop" codon is chosen that is compatible with the artificial genetic code used to encode the unnatural polymer. For example, the "stop" codon should not conflict with any other codons used to encode the synthesis, and it should be of the same general format as the other codons used in the template. The "stop" codon may encode for a monomer unit that terminates polymerization by not providing a reactive group for further attachment. For example, a stop monomer unit may contain a blocked reactive group such as an acetamide rather than a primary amine. In yet other embodiments, the stop monomer unit comprises a biotinylated terminus providing a convenient way of terminating the polymerization step and purifying the resulting polymer.

In one embodiment, mutagenized DNA products are used directly as the template for in vitro synthesis of the corresponding mutant proteins. Because of the high efficiency with which all 19 amino acid substitutions can be generated at a single residue, it is possible to perform saturation mutagenesis on numerous residues of interest, either independently or in combination with other mutations within the protein. As used herein, "complete saturation" mutagenesis is defined as replacing a given amino acid within a protein, with the other 19 naturally-occurring amino acids. For example, gene site saturation mutagenesis, which systematically explores minimally all possible single amino acid substitutions along a protein sequence, is disclosed in Kretz et al., Methods in Enzymology, 2004, 388:3-11; Short, U.S. Pat. No. 6,171,820; and Short, U.S. Pat. No. 6,562,594, each of which is incorporated herein by reference.

In one aspect, this invention provides for the use of codon primers (containing a degenerate N,N,G/T sequence) to introduce point mutations into a polynucleotide, so as to generate a set of progeny polypeptides in which a full range of single amino acid substitutions is represented at each amino acid position (see U.S. Pat. No. 6,171,820; see also, U.S. Pat. No. 5,677,149, each incorporated herein by reference). The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

Codon usage is one of the important factors in eukaryotic gene expression. The frequencies with which different codons are used vary significantly between different hosts, and between proteins expressed at high or low levels within the same organism. The most likely reason for this variation is that preferred codons correlate with the abundance of cognate tRNAs available within the cell. It is possible that codon usage and tRNA acceptor concentrations have coevolved, and that the selection pressure for this coevolution is more pronounced for highly expressed genes than genes expressed at low levels.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In another aspect, the present invention provides for the use of degenerate cassettes having less degeneracy than the N,N,G/T sequence. For example, it may be desirable in some instances to use (e.g., in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence.

It is appreciated, however, that the use of a degenerate N,N,G/T triplet as disclosed herein is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the instant invention provides a way to systematically and fairly easily generate 2000 distinct species (i.e., 20 possible amino acids per position×100 amino acid positions). It is appreciated that there is provided, through the use of an oligo containing a degenerate N,N,G/T triplet, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

Thus, in a preferred embodiment, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a change in property (when compared to the template polypeptide), it can be sequenced to identify the amino acid substitution responsible for such change contained therein.

The template polypeptide may be any protein, however proteins which have a convenient assay for activity such as catalytic activity or ligand binding are preferred. As used herein, a ligand is any molecule which binds specifically to a larger one, such as small molecule binding to a protein. Representative examples of target interactions include catalysis, enzyme-substrate interactions, protein-nucleic acid interactions, receptor-ligand interactions, protein-metal interactions and antibody-antigen interactions. Representative target proteins include enzymes, antibodies, cytokines, receptors, DNA binding proteins, chelating agents, and hormones.

Any chemical synthetic or recombinant mutagenic method may be used to generate the population of mutant polypeptides. The practice of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Cabs eds., 1987, Cold Spring Harbor Laboratory); Methods In Enzymnology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embiyo, (Cold Spring Harbor Laboratory Press, Cold Spring Harbor, N.Y., 1986).

In one embodiment, the template polypeptide is an antibody. The antibody is subjected to the methods described herein to, for example, map and understand which positions within the CDR effect binding affinity. The techniques for preparing and using various antibody-based constructs and fragments thereof are well known in the art. An important aspect of the present invention is the identification of residues that play, or are likely to play, a role in the interaction of interest (e.g., antigen-antibody interaction, metal chelation, receptor binding, substrate binding, etc). Any antibody or antibody fragment may be used according to the present invention.

In one embodiment, any of the evolution platforms CPE, CPI, CPD and CPS can be utilized for generating agonist antibodies, i.e. activating antibodies. These evolution technologies enable the generation of agonist antibodies beyond simpler protein crosslinking type activation and in particular allow the activation of receptors such as GPL-1 or 2 that are traditionally activated by peptides.

In one aspect, antibodies are selected by FACS or microscopy or equivalent for weakly activating antibodies by using cells with fluorescent signals that fluoresce when the cell surface receptor is activated. Subsequently, the evolution tools are used to enhance this activation. The CPS technology is then utilized to combine up-mutants.

In another aspect, an antibody is selected that binds the receptor activation site as determined by epitope mapping. CPE, CPI and/or CPD techniques are used to select for mutants that cause stimulation of the receptor as determined by an intracellular read-out such as fluorescence in response to calcium ion release or other assays that are well known in the art. The CPS technology is then utilized to combine up-mutants.

In a particular aspect, some of the key advantages of CPI with single, double or triple amino acid insertions are that these inserted amino acids can extend into the binding pocket of the receptor to activate the receptor. In another particular aspect, CPD can remodel and/or reposition amino acids interacting with the receptor to improve or effect activation and finally CPE can perform relatively smaller changes to effect receptor activation.

The specificity of an antibody is determined by the complementarity determining regions (CDRs) within the light chain variable regions (VL) and heavy chain variable regions (VH). The Fab fragment of an antibody, which is about one-third the size of a complete antibody contains the heavy and light chain variable regions, the complete light chain constant region and a portion of the heavy chain constant region. Fab molecules are stable and associate well due to the contribution of the constant region sequences. However, the yield of functional Fab expressed in bacterial systems is lower than that of the smaller Fv fragment which contains only the variable regions of the heavy and light chains. The Fv fragment is the smallest portion of an antibody that still retains a functional antigen binding site. The Fv fragment has the same binding properties as the Fab, however without the stability conferred by the constant regions, the two chains of the Fv can dissociate relatively easily in dilute conditions.

In one aspect, VH and VL regions can be fused via a polypeptide linker (Huston et al., 1991) to stabilize the antigen binding site. This single polypeptide Fv fragment is known as a single chain antibody (scFv). The VH and VL can be arranged with either domain first. The linker joins the carboxy terminus of the first chain to the amino terminus of the second chain.

One of skill in the art will recognize that single chain Fv, heavy or light chain Fv or Fab fragments may be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Generally, a single-chain expression polynucleotide is generated. This expression polynucleotide contains: (1) a single-chain antibody cassette consisting of a $V_H$ domain, spacer peptide, and $V_L$ domain operably linked to encode a single-chain antibody, (2) a promoter suitable for in vitro transcription (e.g., T7 promoter, SP6 promoter, and the like) operably linked to ensure in vitro transcription of the single-chain antibody cassette forming a mRNA encoding a single-chain antibody, and (3) a transcription termination sequence suitable for functioning in an in vitro transcription reaction. Optionally, the expression polynucleotide may also comprise an origin of replication and/or a selectable marker. An example of a suitable expression polynucleotide is pLM166.

The $V_H$ and $V_L$ sequences can be conveniently obtained from a library of $V_H$ and $V_L$ sequences produced by PCR amplification using V gene family-specific primers or V gene-specific primers (Nicholls et al., J. Immunol. Meth., 1993, 165: 81; WO93/12227) or are designed according to standard art-known methods based on available sequence information. Typically, mouse or human $V_H$ and $V_L$ sequences are isolated. The $V_H$ and $V_L$ sequences are then ligated, usually with an intervening spacer sequence (e.g., encoding an in-frame flexible peptide spacer), forming a cassette encoding a single-chain antibody. Typically, a library comprising a plurality of $V_H$ and $V_L$ sequences is used (sometimes also with a plurality of spacer peptide species represented), wherein the library is constructed with one or more of the $V_H$ and $V_L$ sequences mutated to increase sequence diversity particularly at CDR residues, sometimes at framework residues. V region sequences can be conveniently cloned as cDNAs or PCR amplification products for immunoglobulin-expressing cells. For example, cells from human hybridoma, or lymphoma, or other cell line that synthesizes either cell surface or secreted immunoglobulin may be used for the isolation of polyA+RNA. The RNA is then used for the synthesis of oligo dT primed cDNA using the enzyme reverse transcriptase (for general methods see, Goodspeed et al., Gene 1989, 76: 1; Dunn et al., J. Biol. Chem., 1989, 264: 13057). Once the V-region CDNA or PCR product is isolated, it is cloned into a vector to form a single-chain antibody cassette.

To accomplish construction of antibodies and antibody fragments, the encoding genes are isolated and identified. The genes can be modified to permit cloning into an expression vector or an in vitro transcription/translation. Although methods can be used such as probing the DNA for VH and VL from hybridoma cDNA (Maniatis et al., 1982) or constructing a synthetic gene for VH and VL (Barbas et al., 1992), a convenient mode is to use template directed methods to amplify the antibody sequences. A diverse population of antibody genes can be amplified from a template sample by designing primers to the conserved sequences at the 3' and 5' ends of the variable region known as the framework or to the constant regions of the antibody (Iverson et al., 1989). Within the primers, restriction sites can be placed to facilitate cloning into an expression vector. By directing the primers to these conserved regions, the diversity of the antibody population is maintained to allow for the construction of diverse libraries. The specific species and class of antibody can be defined by the selection of the primer sequences as illustrated by the large number of sequences for all types of antibodies given in Kabat et al., 1987, hereby incorporated by reference.

Messenger RNA isolated from the spleen or peripheral blood of an animal can be used as the template for the amplification of an antibody library. In certain circumstances, where it is desirable to display a homogeneous population of antibody fragments on the cell surface, mRNA may be isolated from a population of monoclonal antibodies. Messenger RNA from either source can be prepared by standard methods and used directly or for the preparation of a cDNA template. Generation of mRNA for cloning antibody purposes is readily accomplished by following the well-known procedures for preparation and characterization of antibodies (see, e.g., Antibodies: A Laboratory Manual, 1988; incorporated herein by reference).

Generation of monoclonal antibodies (MAbs) follows generally the same procedures as those for preparing polyclonal antibodies. Briefly, a polyclonal antibody is prepared by immunizing an animal with an immunogenic composition in accordance and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, rabbits are usually preferred for production of polyclonal antibodies.

Immunogenic compositions often vary in immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Recognized means for conjugating a polypeptide to a carrier protein are well known and include glutaraldehyde, m-maleimidobenzoyl-N-hydroxysuccinimide ester, carbodiimides and bis-diazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated, stored and the spleen harvested for the isolation of mRNA from the polyclonal response or the animal can be used to generate MAbs for the isolation of mRNA from a homogeneous antibody population.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g. a small molecule hapten conjugated to a carrier, a purified or partially purified protein, polypeptide or peptide. The immunizing composition is administered in a manner effective to stimulate antibody producing cells. Rodents such as mice and rats are frequently used animals; however, the use of rabbit, sheep frog cells is also possible. The use of rats may provide certain advantages (Goding, pp. 60-61, 1986), but mice are preferred, particularly the BALB/c mouse as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from blood samples. Spleen cells and blood cells are preferable, the former because they are a rich source of antibody-producing cells that are in the dividing plasmablast stage, and the latter because blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al., 1977). The use of electrically induced fusion methods is also appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Simple and rapid assays include radioimmunoassays, enzyme immunoassays, cytotoxicity assays, plaque assays, dot immunobinding assays, and the like.

The selected hybridomas are serially diluted and cloned into individual antibody-producing cell lines from which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Following the isolation and characterization of the desired monoclonal antibody, the mRNA can be isolated using techniques well known in the art and used as a template for amplification of the target sequence.

A number of template dependent processes are available to amplify the target sequences before and after mutagenesis. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of target amplified. Polymerase chain reaction methodologies are well known in the art. Using enzymatic amplification techniques such as PCR, desired control elements may be designed into the primer and thus, will be incorporated into the DNA product.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as an amplification method. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having a 3' and 5' sequences of non-specific DNA and middle sequence of specific RNA is hybridized to DNA which is present in a sample. Upon hybridization, the reaction is treated with RNaseH, and the products of the probe identified as distinctive products which are released after digestion. The original template is annealed to another cycling probe and the reaction is repeated.

Other amplification methods are described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Kienow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; O'Hara et al., 1989).

Methods based on ligation of two (or more) oligonucleotides in the presence of nucleic acid having the sequence of the resulting "di-oligonucleotide," thereby amplifying the di-oligonucleotide, also may be used in the amplification step (Wu et al., 1989).

Amplification products may be analyzed by agarose, agarose-acrylamide or polyacrylamide gel electrophoresis using standard methods (see, e.g., Maniatis et al., 1982). For example, one may use a 1% agarose gel stained with ethidium bromide and visualized under UV light. Alternatively, the amplification products may be integrally labeled with radio- or fluorometrically-labeled nucleotides. Gels can then be exposed to x-ray film or visualized under the appropriate stimulating spectra, respectively.

Mutagenic procedures of the present invention may comprise any mutagenic approach that may be tailored to a particular site in a gene, i.e., site-directed or site-specific mutagenesis. Because the present invention relies on comprehensive mutagenesis, the present invention contemplates as preferred embodiments those mutagenic procedures that are rapid, efficient and cost effective.

In one embodiment, the mutagenic procedure utilizes chemical synthesis techniques. In so doing, it is possible to exactly place the substitution at one or more particular locations within the gene, and also to specifically define the nature of the alterations. Chemical synthesis methods for DNA are well known within the art. Solid phase techniques are preferred in this regard.

One advantage to the solid phase method of gene synthesis is the opportunity for mutagenesis using combinatorial synthesis techniques. Combinatorial synthesis techniques are defined as those techniques producing large collections or libraries of compounds simultaneously, by sequentially linking different building blocks. Libraries can be constructed using compounds free in solution, but preferably the compound is linked to a solid support such as a bead, solid particle or even displayed on the surface of a microorganism.

Several methods exist for combinatorial synthesis (Holmes et al., 1995; Burbaum et al., 1995; Martin et al., 1995; Freier et al., 1995; Pei et al., 1991; Bruce et al., 1995; Ohlmeyer et al., 1993), including split synthesis or parallel synthesis. Split synthesis may be used to produce small amounts of a relatively large number of compounds, while parallel synthesis will produce larger amounts of a relatively small number of compounds. In general terms, using split synthesis, compounds are synthesized on the surface of a microparticle. At each step, the particles are partitioned into several groups for the addition of the next component. The different groups are then recombined and partitioned to form new groups. The process is repeated until the compound is completed. Each particle holds several copies of the same compound allowing for facile separation and purification. Split synthesis can only be conducted using a solid support.

An alternative technique known as parallel synthesis may be conducted either in solid phase or solution. Using parallel synthesis, different compounds are synthesized in separate receptacles, often using automation. Parallel synthesis may be conducted in microtiter plate where different reagents can be added to each well in a predefined manner to produce a combinatorial library. Parallel synthesis is the preferred approach for use with enzymatic techniques. It is well understood that many modifications of this technique exist and can be adapted for use with the present invention. Using combinatorial methods, a large number of mutant gene templates may be synthesized.

Mutants genes also may be generated by semisynthetic methods known in the art (Barbas et al., 1992). Using the conserved regions of an antibody fragment as a framework, variable regions can be inserted in random combinations one or more at a time to alter the specificity of the antibody fragment and generate novel binding sites, especially in the generation of antibodies to antigens not conducive to immunization such as toxic or labile compounds. Along the same lines, a known antibody sequence may be varied by introducing mutations randomly. This may be accomplished by methods well known in the art such as the use of error-prone PCR.

Using the appropriate oligonucleotide primers, PCR is used for the rapid synthesis of the DNA template containing one or more mutations in the binding protein gene. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In certain applications, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM MgCl2, 10 mM dithiothreitol, at temperatures between approximately 20° C. to about 37° C. Other hybridization conditions utilized could include approximately 10 mM Tris-HCl (pH 8.3), 50 mM KCl, 1.5 μM MgCl2, at temperatures ranging from approximately 40° C. to about 72° C. Formamide and SDS also may be used to alter the hybridization conditions.

In a particular embodiment, overlap PCR may be employed. Briefly, a plasmid is used as a template for the first round of PCR. The PCR products from the first round are purified and used, together with outside primers, in the overlap extension PCR reaction. The end products contained the site directed replacement of a given amino acid with all other possible amino acid residues.

The mutagenized DNA template for the polypeptide of interest can be cloned into a plasmid for in vitro transcription/translation or in the preferred embodiment, the appropriate control elements are included within the PCR product for direct in vitro transcription/translation. In vitro transcription/translation of genes uses cell free extracts to provide the required enzymes, ribosomes and protein factors. The synthesis of proteins is directed by mRNA synthesized from the desired DNA templates. The DNA template must contain the appropriate control elements for the system used including a ribosome binding site and promoter sequence. One of skill in the art would clearly recognize the appropriate required elements for each system.

Prokaryotic in vitro techniques for protein production were the first to be used (Zubay et al., 1970). Subsequently eukaryotic systems were developed using wheat germ (Roberts, 1973) and rabbit reticulocytes (Pelham, 1976). Several new developments have increased the efficiency of these techniques. Examples include, the development of nuclease deficient strains of E. coli to improve the results using linear DNA templates (Yang, 1980) and treatment of reticulocyte lysates with micrococcal nuclease to lower any background expression from the system.

The most recent systems developed for in vitro transcription/translation are based on transcription by phage RNA polymerases including SP6 and SP7 (Krieg, 1987, Studier, 1990). DNA placed under the control of T7 promoter elements can be used as a template for in vitro transcription by T7 RNA polymerase or for complete in vitro transcription/translation with the polymerase added to either a prokaryotic or eukaryotic protein synthesis system. While the methods of the present invention can be used with any in vitro transcription/translation system, the T7 system is preferred for transcription and the use of a prokaryotic translation system is preferred as no capping of the RNA is required.

Using in vitro methods for translation, amino acid derivatives may be incorporated into the protein by addition of the derivatized amino acid to the protein synthesis system mixture. Varying the concentration of the derivatives, with respect to the normal amino acid, permits one to create a mixed population and measure relative effects.

Mutant polypeptides generated by the present invention may be characterized using a variety of techniques. In general, protein products may be analyzed for the correct apparent molecular weight using SDS-PAGE. This provides an initial indication that the polypeptide was, in fact, synthesized. When compared to the natural molecule, it also indicates whether normal folding or processing is taking place with the mutant. In this regard, it may prove useful to label the polypeptide. Alternatively, the polypeptide may be identified by staining of the gel.

Beyond mere synthesis, proteins may be characterized according to various properties and an extensive range of functions. Properties include isoelectric point, thermal stability, sedimentation rate and folding. One manner of examining folding is the ability to be recognized by a cognate binding partner. The prime example of this function is the antibody-antigen interaction. A wide variety of different immunoassay formats are available for this purpose and are well known in the art. Principally, changes in either affinity or specificity can be determined when the protein is contacted with a specific ligand or panels of related ligands.

Immunoassays can be generally divided into two types: heterogeneous assays requiring multiple separation steps, and homogeneous assays which are performed directly. Heterogeneous immunoassays in general involve a ligand or antibody immobilized on a solid matrix. A sample containing a ligand is contacted with the immobilized antibody and the amount of complex formed on the matrix support is determined from a label attached directly or indirectly to the immobilized complex. As used in the context of the present invention, ligand is defined as a species that interacts with a non-identical molecule to form a tightly bound, stable complex. For practical purposes, the binding affinity is usually greater than about $10^6$ $M^{-1}$ and is preferably in the range of $10^9$-$10^{15}$ $M^{-1}$. The ligand may be any of several types of organic molecules, including alicyclic hydrocarbons, polynuclear aromatics, halogenated compounds, benzenoids, polynuclear hydrocarbons, nitrogen heterocyclics, sulfur heterocyclics, oxygen heterocyclics, and alkane, alkene alkyne hydrocarbons, etc. Biological molecules are of particular interest, including amino acids, peptides, proteins, lipids, saccharides, nucleic acids and combinations thereof. Of course it will be understood that these are by way of example only and that contemplated immunoassay methods are applicable to detecting an extraordinarily wide range of compounds, so long as one can obtain an antibody that binds with the ligand of interest.

Heterogeneous immunoassays may be performed as sandwich assays in which a molecule of interest is reacted with an immobilized antibody that specifically binds that molecule with high affinity. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of ligand in the sample, is measured.

Detection of immunocomplex formation is well known in the art and may be achieved through the application of numerous approaches. These approaches are typically based upon the detection of a label or marker, such as any of the radioactive, fluorescent, chemiluminescent, electrochemiluminescent, biological or enzymatic tags or labels known in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Preferred methods for detection includes radioimmunoassay (RIA) or enzyme-linked immunosorbent assay (ELISA) with ELISA being most preferred due to generally increased sensitivity. ELISAs are extensively used in biotechnology applications, particularly as immunoassays for a wide range of antigenic substances. The sensitivity of ELISA is based on the enzymatic amplification of the signal Other preferred proteins contemplated for use in accordance with the present invention are those which have a convenient assay for activity. Representative examples of target interactions include catalysis, enzyme-substrate interactions, protein-nucleic acid interactions, receptor-ligand interactions and protein-metal interactions. In these assays the mutant proteins can be compared with the wild-type protein for changes in the ability to perform any of the foregoing functions.

As used herein, the term "contacting" is defined as bringing the reaction components into close enough proximity to each other to allow the desired interaction to occur. Contacting may be accomplished by mixing the components in solution, for example, or by heterogeneous interaction such as by flow contact through a column or immobilizing matrix that binds to one of the components.

For mutant proteins having a catalytic activity, the appropriate reaction may be monitored for a change in catalytic rate or an alteration in specificity.

The antibodies produced and isolated by the method of the invention are selected to bind a predetermined target. Typically, the predetermined target will be selected in view of its applicability as a diagnostic and/or therapeutic target. The predetermined target may be a known or unknown epitope Antibodies generally bind to a predetermined antigen (e.g., the immunogen) with an affinity of about at least $1\times10^7$ M$^{-1}$, preferably with an affinity of about at least $5\times10^7$ M$^{-1}$ more preferably with an affinity of at least $1\times10^8$ M$^{-1}$ to $1\times10^9$ M$^{-1}$ or more, sometimes up to $1\times10^{10}$ M$^{-1}$ or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

In another example, several reports of the diagnostic and therapeutic utility of scFv have been published (Gruber et al., 1994 op.cit.; Lilley et al., 1994 op.cit.; Huston et al., Int. Rev. Immunol 1993, 10:a 195, Sandhu J S, Crit. Rev. Biotechnol., 1992,12: 437).

High affinity antibodies of the desired specificity can be engineered and expressed in a variety of systems. For example, scFv have been produced in plants (Firek et al. (1993) Plant Mol. Biol. 23: 861) and can be readily made in prokaryotic systems (Owens RJ and Young RJ, J. Immunol. Meth., 1994,168: 149; Johnson S and Bird RE, Methods Enzymol., 1991, 203: 88). Furthermore, the single-chain antibodies can be used as a basis for constructing whole antibodies or various fragments thereof (Kettleborough et al., Euro J. Immunol., 1994, 24: 952). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a eukaryotic cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are preferred, because a number of suitable host cell lines capable of secreting intact immunoglobulins have been developed in the art, and include the CHO cell lines, various COS cell lines, HeLa cells, myeloma cell lines, B-cells or hybridomas. Expression vectors for these cells can include expression control sequences, such as an origin of replication, a promoter, an enhancer (Queen et al., Immunol. Rev. 1986, 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 30 obp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and microinjection (see, generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., Protein Purification, Springer-Verlag, N.Y. (1982)). Once purified, partially or to homogeneity as desired, the polypeptides may then be used therapeutically or in developing and performing assay procedures, immunofluorescent stainings, and the like (see, generally, Immunological Methods, Vols. I and II, Eds. Lefkovits and Pernis, Academic Press, N.Y. N.Y. (1979 and 1981)).

The oligopeptides of the present invention can be used for diagnosis and therapy. By way of illustration and not limitation, antibodies can be used to treat cancer, autoimmune diseases, or viral infections. For treatment of cancer, the antibodies will typically bind to an antigen expressed preferentially on cancer cells, such as erbB-2, CEA, CD33, and many other antigens well known to those skilled in the art. For treatment of autoimmune disease, the antibodies will typically bind to an antigen expressed on T-cells, such as CD4, the IL-2 receptor, the various T-cell antigen receptors and many other antigens well known to those skilled in the art (e.g., see Fundamental Immunology, 2nd ed., W. E. Paul, ed., Raven Press: New York, N.Y., which is incorporated herein by reference). For treatment of viral infections, the antibodies will typically bind to an antigen expressed on cells infected by a particular virus such as the various glycoproteins (e.g., gB, gD, gE) of herpes simplex virus and cytomegalovirus, and many other antigens well known to those skilled in the art (e.g., see Virology, 2nd ed., B. N. Fields et al., eds., (1990), Raven Press: New York, N.Y.).

Pharmaceutical compositions comprising antibodies of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the mutant antibodies in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of mutant antibody. A typical composition for intravenous infusion can be made up to contain 250 ml of sterile Ringer's solution, and 10 mg of mutant antibody. Actual methods for preparing parenterally administrable compositions will be known or apparent to those skilled in the art and are described in more detail in, for example, Remington's Pharmaceutical Science, 20th Ed., Mack Publishing Company, Easton, Pa. (2000), which is incorporated herein by reference.

Manufacturing of Candidates and/or Evolved Candidates

In one embodiment, the eukaryotic system is a mammalian system selected from one of the group consisting of CHO, HEK293, IM9, DS-1, THP-1, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC.

In one embodiment, a variety of mammalian host cells can be used in the manufacturing of candidate, including Fibroblast cells (3T3, mouse; BHK21, Syrian hamster) Epithelial cells (MDCK, dog; Hela, human; PtK1, rat kangaroo) Plasma cells ((SP2/0 and NS0, mouse) Kidney cells (293, human; COS, monkey) Ovary cells (CHO, Chinese hamster) Embryonic cells (R1 and E14.1, mouse; H1 and H9, human; PER C.6, human).

In certain aspects, the recombinant antibodies are produced in CHO and NS0 and SP2/0 cell lines. In a specific aspect, the mammalian system is a CHO-S cell line. Expression vector systems most frequently used are glutamine synthetase expression systems and others based on Dihydrofolate reductase genes.

In another embodiment, the eukaryotic system is a yeast cell system. In one aspect, the yeast cell system is selected from *S. cerevisiae* or *picchia* cells.

In the method of the present invention, hosts used for screening evolved molecules are the same as hosts used for downstream manufacturing of hits. In another aspect of the present invention, the genetic system used for discovery and evolution of proteins is exactly the same as the genetic system used for manufacturing the protein for commercial applications.

Biosimilars

Biosimilars are protein based therapeutics that have an identical amino acid sequence (i.e. chemical composition) as an approved ethical drug which is no longer patent protected. In one aspect, the CIAO method is particularly relevant for biosimilars. While it is essential to produce the protein therapeutic in an equivalent formulation and composition, to be competitive in the marketplace the biosimilar should be made quickly and as cheaply as possible. Cell culture media and process development are some of the most costly and time consuming parts of preparing and producing a biosimlar.

Changing the silent mutation codons within a protein therapeutic changes the codon used for protein translation but preserve the amino acid sequence within the protein. These codon changes at a variety of positions within a molecule, particularly in the amino terminus can have significant impact on expression and in some cases even glycosylation. In one aspect, the CIAO method is used to select and evolve the silent mutation codons in a protein within a host cell similar to the one ultimately used for manufacturing. Therefore processing time can be reduced due to the higher protein yields and the fact that the protein was selected to express in the host cell line, so most traditional manufacturing issues have been selected out of the molecule. Further, by selecting the molecules in inexpensive, serum free culture media, molecules can be selected with codons that permit inexpensive manufacturing and purification.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLES

Example 1

Generation and Screening of an Antibody Library

This example describes the method of generating and screening a mammalian cell surface display human antibody library to isolate human antibodies with binding activity to a target antigen using the combination of flow cytometric sorting and ELISA.

Library Screening by Flow Cytometric Analysis
1. Generate human antibody libraries stably integrated in mammalian cells such as described in Appendix 1.2, 1.3 and 1.4 below.
2. Expand stable fully human antibody library clones prior to flow cytometric analysis.
3. On the day of flow cytometric analysis, wash $1 \times 10^7$ cells with 1×PBS
4. Detach cell with Detachin cell detachment medium and collect cells in 1×PBS 5. Spin down cells at 3000 rpm for 5 minutes. Remove supernatant.
6. Re-suspend cell pellet in 1 ml of cold 1×PBS and spin at 3000 rpm for 5 minutes.
7. Remove supernatant and re-suspend the cell pellet in 500 µl of 2 µg/ml of purified human 001 protein in cold 1×PBS.
8. Incubate on ice for 1 hour with occasionally mixing by hand.
9. Spin down cells at 3000 rpm for 5 minutes. Remove supernatant.
10. Re-suspend cell pellet in 1 ml of cold 1×PBS and spin at 3000 rpm for 5 minutes.
11. Repeat steps 7 and 8.
12. Remove supernatant and re-suspend the cell pellet in 500 µl of 1 µg/ml of rabbit anti-human 001 polyclonal antibody in cold 1×PBS with 10% goat serum.
13. Incubate on ice for 30 minute with occasionally mixing by hand.
14. Spin down cells at 3000 rpm for 5 minutes. Remove supernatant.
15. Re-suspend cell pellet in 1 ml of cold 1×PBS and spin at 3000 rpm for 5 minutes.
16. Repeat steps 7 and 8.
17. Remove supernatant and re-suspend the cell pellet in 500 µl of goat anti-rabbit antibody conjugate with FITC and goat anti-human Fc antibody conjugate with pyroerthrin in cold 1×PBS with 10% goat serum.
18. Incubate on ice for 30 minute with occasionally mixing by hand.
19. Spin down cells at 3000 rpm for 5 minutes. Remove supernatant.
20. Re-suspend cell pellet in 1 ml of cold 1×PBS and spin at 3000 rpm for 5 minutes.
21. Repeat steps 7 and 8.
22. Remove supernatant and re-suspend the cell pellet in 1 ml of cold 1×PBS with 2% goat serum.
23. Proceed with flow cytometric analysis using Dako MoFlo.
24. Draw a sort window to include the top 0.1% of total cells in terms of ratio of PE/FITC fluorescence. Collect cells that fall within the sort window in 96 well plates with 100 µl of growth media.

Recovery of Heavy Chain and Light Chain Variable Region Sequences

1. Expand the clones from 96 well plates to 6 well plates. When the cells reach 80% confluence in the 6 well plates, proceed to genomic DNA isolation using Qiagen DNeasy Tissue kit.
2. Aspirate off the media from the cells. Add 500 ml of 1×PBS to each 6 well. Scrap the cells off the plate with sterile pipet tips. Transfer scrapped cells in PBS to a sterile micro-centrifuge tube.
3. Centrifuge the cells for 5 minutes at 3000 rpm.
4. Remove supernatant and re-suspend cell pellet in 200 µl 1×PBS.
5. Add 20 µl proteinase K and 200 µl Buffer AL to the sample, mix thoroughly by vortexing, and incubate at 56° C. for 10 minutes.
6. Add 200 µl ethanol to the sample and mix thoroughly by vortexing.
7. Pipet the mixture from step 6 into a spin column Centrifuge at 8000 rpm for one minute. Discard the flow-through.
8. Add 500 µl Buffer AW1 and centrifuge for one minute at 8000 rpm. Discard the flow-through.
9. Add 500 µl Buffer AW2 and centrifuge for 2 minutes at 14,000 rpm. Discard the flow-through. Centrifuge again for one minute at 14,000 rpm. Make sure the membrane is completely dry.
10. Place the spin column in a sterile micro-centrifuge tube and pipet 200 µl Buffer AE directly onto the membrane.
11. Incubate at room temperature for one minute and centrifuge for one minute at 8000 rpm to elute the genomic DNA.
12. QC the genomic DNA by setting up the following reactions in 1.5 ml micro-centrifuge tubes:

| | |
|---|---|
| gDNA | 5 µl |
| 10x Sample loading buffer | 5 µl |
| Total Volume | 10 µl |

Load onto a 0.8% agarose TAE gel with 0.5 µg/ml Ethidium Bromide. Use 1 kB DNA ladder as standard. Run the gel at 100V for 20-30 minutes in 1×TAE buffer.

13. Set up the following PCR reactions in sterile PCR tubes:

| | |
|---|---|
| gDNA | 1 µl |
| 2x HotStar Taq Master Mix | 12.5 µl |
| Variable domain forward primer* | 0.5 µl |
| Variable domain reverse primer* | 0.5 µl |
| H2O | 10.5 µl |
| Total Volume | 25 µl |

*see appendix 1.2

14. Place the PCR tubes in the thermal cycler and start the cycling program.
Initial activation step: 15 minutes, 95° C.
3-step cycling
Denaturation: 40 seconds, 94° C.
Annealing: 40 seconds, 55° C.
Extension: 2 minutes, 72° C.
Number of cycles: 30
Final extension step: 10 minutes, 72° C.
15. QC the PCR reactions by setting up the following reactions in 1.5 ml micro-centrifuge tubes:

| | |
|---|---|
| PCR reaction | 5 µl |
| 10x Sample loading buffer | 5 µl |
| Total Volume | 10 µl |

Load onto a 1% agarose TAE gel with 0.5 µg/ml Ethidium Bromide. Use 1kB DNA ladder as standard. Run the gel at 100V for 20-30 minutes in 1×TAE buffer.

16. Set up the following cloning reactions in 1.5 ml micro-centrifuge tubes using Invitrogen TOPO 2.1 kit:

| | |
|---|---|
| PCR reaction | 4 µl |
| Salt Solution | 1 µl |
| TOPO vector | 1 µl |
| Total Volume | 6 µl |

17. Mix reactions gently and incubate for 5 minutes at room temperature.
18. Add 2 µl of the TOPO cloning reaction from step 17 into a vial of One Shot Chemically competent *E. coli* and mix gently.

19. Incubate on ice for 30 minutes.
20. Heat-shock the cells for 30 seconds at 42° C.
21. Transfer the tubes to ice and incubate for 2 minutes.
22. Add 250 µl of room temperature S.O.C. medium.
23. Shake the tubes horizontally at 37° C. for one hour at 200 rpm.
24. Spread 10 µl of the transformation on a re-warmed LB-carbenicillin plate.
25. Incubate plate overnight at 37 C.
26. Pick 6 clones from each transformation for sequencing.
27. Analyze the heavy chain and light chain variable region sequences. Proceed to the second round of screening using the ELISA method.

Digest Vector and Human Antibody Clones with Restriction Enzymes

Reactions will depend on restriction enzyme(s) chosen, and according to manufacturer's instructions; examples are provided here: Prepare the following digestion reactions in a microcentrifuge tube on ice:

| | |
|---|---|
| Vector DNA (2 µg) | x µl |
| 10X Rest Enz Buffer x | 10 µl |
| Nuclease-free water | QS to 97 µl |
| Rest Enz 1 (10 U/µl) | 3 µl |
| Rest Enz 2 (10 U/µl) | 3 µl |
| Total reaction volume | 100 µl |
| Human antibody clones (5 ug) | x µl |
| 10X Rest Enz Buffer x | 10 µl |
| Nuclease-free water | QS to 97 µl |
| Rest Enz 1 (10 U/µl) | 3 µl |
| Rest Enz 2 (10 U/µl) | 3 µl |
| Total reaction volume | 100 µl |

1. Mix gently and spin briefly (5 sec.) in microfuge
2. Incubate the reaction at 37° C. overnight CIP Digest Vector and Purify with QIAquick PCR Purification Kit 3. Add 2 µl of Apex phosphatase to the microcentrifuge tube containing the vector digestion reaction.
4. Incubate at 37° C. for 10 minutes
5. Heat at 70° C. for 5 minutes to inactivate the Apex phosphatase
6. Add 500 µL of Buffer PBI to the microcentrifuge
7. Mix by vortexing and quick centrifuge
8. Load 750 µL at a time onto a column
9. Centrifuge at 12,000×g for 1 minute and decant liquid from collection tube
10. Repeat until all sample has been processed.
11. Wash with 750 µL PE Buffer (Ethanol added!)
12. Centrifuge at 12,000×g for 1 minute and decant liquid from collection tube
13. Place column back onto collection tube and centrifuge again
14. Put column onto new microcentrifuge tubes and elute with 50 µL EB Buffer.

Gel Purify Restriction Enzyme Digested Human Antibody Clones

1. Set up the following reactions in a 1.5 ml micro-centrifuge tube:

| | |
|---|---|
| Rest Enz digested Fully human antibody clones | 100 µl |
| 10x Sample loading buffer | 3 µl |
| Total Volume | 103 µl |

2. Load onto a 1% agarose TAE gel with 0.5 µg/ml Ethidium Bromide. Use 1kB DNA ladder as standard. Run the gel at 100V for 20-30 minutes in 1×TAE buffer.
3. Cut out the bands corresponding to the heavy chain (HC) and light chain (LC) variable regions and purified using QIAquick Gel Extraction Kit.
4. Add 3 volume of buffer QG to 1 volume of gel.
5. Incubate at 50° C. for 10 minutes until the gel slice has completely dissolved. Add 1 gel volume of isopropanol to the sample and mix.
6. Place a QIAquick spin column in a provided 2 ml collection tube.
7. Apply the sample to the QIAquick column, and centrifuge for 1 minute.
8. Discard flow-through and place QIAquick column back in the same collection tube.
9. Add 0.75 ml of buffer PE to QIAquick column and centrifuge for 1 minute.
10. Discard the flow-through and centrifuge the QIAquick column for an additional 1 minute at 17,900×g (13,000 rpm).
11. Place QIAquick column into a clean 1.5 ml microcentrifuge tube.
12. Add 52 µl of buffer EB to the center of the QIAquick membrane and centrifuge the column for 1 minute. Let the column stand for 1 minute, and then centrifuge for 1 minute.

Ligate Human HC and LC Variable Domain into Digested Vector DNA

Prepare the following ligation reaction in a microcentrifuge tube on ice:

| | |
|---|---|
| Digested vector DNA (100 ng) | x µl |
| Human HC and LC variable domain | y µl |
| 5X T4 ligase Buffer | 4 µl |
| Nuclease-free water | QS to 19 µl |
| T4 ligase (2,000 U/µl) | 1 µl |
| Total reaction volume | 20 µL |

1. Mix gently and spin briefly (5 sec.) in microfuge
2. Incubate at room temperature for 2 hours or 16° C. overnight
3. Transform each of the ligation reaction mixtures into Supercompetent E. coli cells
4. Pre-chill 14 ml BD Falcon polypropylene round-bottom tubes on ice. Prepare SOC medium to 42° C.
5. Thaw the Supercompetent cells on ice. When thawed, gently mix and aliquot 100 ul of cells into each of the pre-chilled tubes.
6. Add 1.7 µl of β-mercaptoethanol to each aliquot of cells. Incubate the cells on ice for 10 minutes, swirling gently every 2 minutes.
7. Add 2 µl of the ligation reaction mixture to one aliquot of cells. Flick the tubes gently.
8. Incubate the tubes on ice for 30 minutes.
9. Heat-pulse the tubes in a 42° C. water bath for 45 seconds.
10. Incubate the tubes on ice for 2 minutes
11. Add 900 µl of preheated SOC medium and incubate the tubes at 37° C. for 1 hour with shaking at 225-250 rpm.
12. Plate 20 µl and 200 µl of the transformation mixture on LB agar plates containing carbenicillin.
13. Incubate the plates at 37° C. overnight.
14. Count colonies on plates and pick 6 colonies for PCR screening and sequencing.
15. Choose one clone with the correct sequence, prepare plasmid DNA, and proceed to transfection in 293F cells.

Transfection of 293F Cells
1. One week before transfection, transfer 293F cells to monolayer culture in serum supplemented Dulbecco's Modified Eagle Medium (D-MEM).
2. One day before transfection, plate $0.1 \times 10^5$ cells in 100 l of serum supplemented D-MEM per transfection sample in 96 well formats.
3. For each transfection sample, prepare DNA-Lipofectamine complexes.
4. Dilute 0.2 μg of DNA in 50 μl Opti-MEM Reduced Serum Medium. Mix gently.
5. Dilute 0.125 μl Lipofecctamine in 50 μl Opti-MEM Reduced Serum Medium. Mix gently and incubate for 5 mM at room temperature.
6. Combine the diluted DNA with the diluted Lipofectamine. Mix gently and incubate for 20 mM at room temperature.
7. Add the 100 μl DNA-Lipofectamine complexes to each well containing cells and medium. Mix gently by rocking the plate back and forth.
8. Incubate the cells at 37° C. in a 5% $CO_2$ incubator.
9. Add 100 μl of serum supplemented D-MEM to each well after 6 hours. Incubate the cells at 37° C. in a 5% $CO_2$ incubator overnight.
10. Aspirate off medium in each well. Wash each well with 100 μl of 293 SFM II with 4 mM L-Glutamine. Add 100 μl of 293 SFM II with 4 mM L-Glutamine to each well.
11. Collect supernatant for ELISA at 96 hours after transfection.

Appendix 1.1: Buffer Recipes
1×PBS with 2% goal serum
2 ml goat serum
98 ml 1×PBS
50×TAE buffer
242 g Tris base
57.1 ml glacial acetic acid
37.2 g $Na_2EDTA-2H_2O$
Add distilled $H_2O$ to final volume of 1 liter
1×TAE buffer
20 ml 50×TAE buffer
800 ml distilled $H_2O$
0.8% Agarose Gel with ethidium bromide
0.8 g LE agarose
100 ml 1×TAE buffer
Melt the agarose in a microwave oven and swirl to ensure even mixing
Cool agarose to 55° C.
Add 2.5 μl of 20 mg/ml Ethidium Bromide to agarose
Pour onto a gel platform
1% Agarose Gel with ethidium bromide
1 g LE agarose
100 ml 1×TAE buffer
Melt the agarose in a microwave oven and swirl to ensure even mixing
Cool agarose to 55° C.
Add 2.5 μl of 20 mg/ml Ethidium Bromide to agarose
Pour onto a gel platform
LB
10 g NaCl
10 g tryptone
5 g yeast extract
Add distilled $H_2O$ to a final volume of 1 liter
Adjust pH to 7.0 with 5 N NaOH
Autoclave
LB-carbenicillin agar
10 g NaCl
10 g tryptone
5 g yeast extract
20 g agar
Add distilled $H_2O$ to a final volume of 1 liter
Adjust pH to 7.0 with 5 N NaOH
Autoclave
Cool to 55° C.
Add 10 ml of 10 mg/ml of filter-sterilized carbenicillin
Pour into petri dishes (25 ml/100-mm plate)
SOC Medium
0.5 g NaCl
20 g tryptone
0.5 g yeast extract
2 ml of filter-sterilized 20% glucose
Add distilled $H_2O$ to a final volume of 1 liter
Autoclave
Add 10 ml of filter-sterilized 1 M $MgCl_2$ and 10 ml of filter-sterilized 1 M $MgSO_s$ prior to use
Washing Solution
0.05% Tween-20 in PBS
Blocking solution
2% Carnation non-fat milk in PBS
Heat inactivated fetal bovine serum
500 ml heat inactivated fetal bovine serum in the original vendor bottle
Heat for 30 minutes at 56° C. with mixing every 5 minutes
Prepare 50 ml aliquots and store at −20° C.
Serum supplemented Dulbecco's Modified Eagle Medium
500 ml Dulbecco's Modified Eagle Medium
50 ml heat inactivated fetal bovine serum
5 ml 10 mM MEM Non-Essential Amino Acids
293 SFM II with 4 mM L-Glutamine
500 ml SFM II
10 ml 200 mM L-Glutamine
DEAE-Dextran solution
1 g DEAE-dextran (diethylaminoethyl-dextran)
Dissolve in 100 ml of distilled water
Filter sterilize Appendix 1.2: Construction of Fully Human Antibody Library All functional human germline heavy chain ($V_H$) and kappa light chain ($V_k$) V regions can be obtained from V base (http://vbase.mrc-cpe.cam.ac.uk/) and aligned. The alignments can then be analyzed regarding diversity, especially in the framework three regions. Desired number of $V_H$ and $V_k$ genes from the resulting sequence clusters can then be selected for library construction.

V Region Cloning

Heavy and light chain V region genes (including Frameworks 1, 2, and 3 and CDR1, CDR2 and CDR3) are amplified from human genomic DNA in two pieces using gene specific primers. Partial V-region genes are then combined by overlap PCR. A linker is added to full length LC V-regions by nested PCR before cloning into mammalian expression vector. Cloned LC variable domains are sequence confirmed (yielding LC V clones). The heavy chain variable domains are TOPO cloned and sequence confirmed (HC V TOPO clones). Sequence confirmed HC V regions are amplified from the corresponding plasmids, a linker is added to the 3' end, and the resulting PCR products are cloned into the LC V variable domain clones to form Vk/VH combinations and into a mammalian vector.

Expression of Full Length IgGs

Expression of full length kappa light chain and IgG1 heavy chain in the desired mammalian vector can be driven from a single promoter, for example, CMV promoter. Each chain is preceded by a secretion signal targeting the nascent polypeptide chain to the endoplasmatic reticulum (ER). An anchoring signal can be fused to the C-terminus of the heavy chain. This signal is cleaved off and replaced with an anchor which attaches the full length IgG to the outside of the cell membrane after secretion.

Appendix 1.3: Generation of Stable Fully Human Antibody Library in Mammalian Cells by Transfection 1. One week before transfection, transfer CHO-S cells to monolayer culture in serum supplemented Dulbecco's Modified Eagle Medium (D-MEM).
2. One day before transfection, plate $6 \times 10^6$ cells in 15 ml of serum supplemented D-MEM per transfection sample in a 10-cm tissue culture plate. Prepare ten 10-cm plates
3. For each 10-cm plate, prepare DNA-Lipofectamine complexes following steps 4-7.
4. Dilute 25 µg of maxi-prep fully human antibody library plasmid DNA in 1.5 ml Opti-MEM Reduced Serum Medium. Mix gently.
5. Dilute 60 µl Lipofecctamine in 1.5 ml Opti-MEM Reduced Serum Medium. Mix gently and incubate for 5 min at room temperature.
6. Combine the diluted DNA with the diluted Lipofectamine. Mix gently and incubate for 20 min at room temperature.
7. Add the 3 ml DNA-Lipofectamine complexes to each plate containing cells and medium. Mix gently by rocking the plate back and forth.
8. Incubate the cells at 37° C. in a 5% $CO_2$ incubator overnight.
9. Medium change each plate with 15 ml of serum supplemented D-MEM. Incubate the cells at 37° C. in a 5% $CO_2$ incubator for 48 hours.
10. Detach cells with Detachin cell detachment medium and re-suspend cells in serum supplemented D-MEM.
11. Plate $0.4 \times 10^6$ cells in 10 ml of serum supplemented D-MEM with 800 µg/ml G418 in one 10-cm tissue culture plate. Transfer all transfected cells resulting in $150 \times 10$-cm plates.
12. Plate $0.4 \times 10^6$ un-transfected CHO-S cells in 10 ml of serum supplemented D-MEM with 800 µg/ml G418 in one 10-cm tissue culture plate.
13. Feed the cells with serum supplemented D-MEM with 800 µg/ml G418 every 4 days.
14. After 14 days, inspect the plates with non-transfected CHO-S cells. There should be no live cells on the plate.
15. Detach the remaining transfected cells with Detachin cell detachment medium and freeze the cells in freezing media at $1 \times 10^7$ cells/ml.

Appendix 1.4: Generation of Stable Fully Human Antibody Library in Mammalian Cells by Retroviral Infection 1. One day before transfection, plate $6 \times 10^6$ EcoPack-2 293 cells in 15 ml of serum supplemented D-MEM per transfection sample in a 10-cm tissue culture plate. Prepare ten 10-cm plates.
2. Prepare the MBS-containing medium. This is done immediatelye prior to the transfection. For each 10-cm tissue culture plate, 12 ml of MBS-containing medium must be prepared.
3. Add 12 ml of MBS-containing medium to each 10-cm plate and return the plates to the plates to the 37° C. incubator. This must be done 20-30 minutes before the addition of the DNA suspension.
4. Resuspend 10 µg maxi-prep fully human antibody library plasmid DNA pellet in 450 µl sterile H2O and transfer the DNA to separate 5-ml BD Falcon polystyrene round-bottom tubes.
5. Add 50 µl of Solution I and 500µ Solution II from the Stratagene Transfection MBS Mammalian Transfection Kit to the DNA.
6. Gently resuspend any precipitate in the DNA suspension by pipetting the suspension up and down with a pipettor set at 500 µl.
7. Incubate the DNA suspension at room temperature for 10 minutes.
8. Remove the 10-cm plates to be transfected from the incubator and add the DNA suspension onto the plates in a dropwise fashion, swirling gently to prevent the cells from being lifted from the plate and to distribute the DNA suspension evenly.
9. Return the tissue culture plates to the 37° C. incubator.
10. After incubating for 3 hours, remove the medium from the plates and replace it with 4 ml of 4 ml serum supplemented D-MEM supplemented with 25 µM chloroquine. Return the plates to the 37° C. incubator.
11. After incubating for an additional 6-7 hours, remove the growth medium containing 25 chloroquine and replace with 4 ml serum supplemented D-MEM without chloroquine.
12. Incubate the plate in the 37° C. incubator overnight.
13. Remove medium from the plates and replace with 3.0 ml of fresh serum supplemented D-MEM. Return the plates to the 37° C. incubator.
14. Remove the virus-producing packaging cells from the incubator.
15. Collect the virus-containing supernatant from the first plate and filter it through a 0.45 µm filter into a sterile 50-ml conical tube.
16. Aliquot the viral supernatant into 1.5 ml cryovials and snap freeze in dry ice/ethanol bath. Store the viral supernatant at –80° C.
17. Plate $0.5 \times 10^6$ NIH-3T3 cells in 10 ml of serum supplemented D-MEM in one 10-cm tissue culture plate. Plate $102 \times 10$-cm tissue culture plates.
18. Quickly thaw the supernatant by rapid agitation in a 37° C. H2O bath.
19. Dilute the virus in calf serum supplemented DMEM with DEAE-dextran solution at the titer of $0.3 \times 10^5$ viral particle/ml. Prepare 3 ml diluted virus per 100-mm plate to be infected (20% of the cells will be infected). Prepared "mock cocktail" of growth medium plus DEAE-dextran to be used as the negative control.
20. Aspirate off medium from NIH-3T3 cells. For each plate, spread 3.0 ml diluted virus evenly over the cells. Return the plates to the 37° C. incubator for 3 hours.
21. After the 3 hour incubation, add an additional 7.0 ml calf serum supplemented D-MEM to each plate, and return the plates to the 37° C. incubator. Incubate the plate for 48 hours.
22. Replace medium with 10 ml of calf serum supplemented D-MEM with 800 µg/m G418 in each 10-cm tissue culture plate.
23. Feed the cells with calf serum supplemented D-MEM with 800 µg/ml G418 every 4 days.
24. After 14 days, inspect the plates with mock-infected NIH-3T3 cells. There should be no live cells on the plate.
25. Detach the remaining transfected cells with Detachin cell detachment medium and freeze the cells in freezing media at $1 \times 10^7$ cells/ml.

Example 2

Reactions for Comprehensive Positional Evolution (CPE) Mutagenesis reaction

One pair of primers (Primer mix 1 and Primer mix 2) is designed for each codon to be inserted. Design will depend on gene sequence, and sequence analysis databases such as Sequencher (Gene Codes Corporation) or VectorNTl® (Life Technologies) can be used to design the primers. For CPE, one pair of primers is designed for each codon to be mutated. A degenerate target codon (NNK or NNN) is in the middle, flanked by 20 bases on each side (total primer length: 43 bases, 9f clones for sequencing to identify unique mutants). Template DNA is vector DNA with target gene(s).

Prepare the following reactions in 96-well thin wall PCR plates or 0.2 ml thin wall PCR tubes on ice:

| | |
|---|---|
| Primer mix 1 (2.5 µM) | 5 µl |
| Primer mix 2 (2.5 µM) | 5 µl |
| 10X Pfu turbo DNA polymerase buffer | 2.5 µl |
| DNA template (5, 10, 25 ng) | x µl |
| dNTPs | 2 µl |
| Nuclease-free water | QS to 24.5 µl |
| Pfu turbo DNA polymerase (2.5 U/µl) | 0.5 µl |
| Total reaction volume | 25 µl |

1. Prepare one negative control reaction per one 96-well plate (replace primers with TE buffer)
2. Mix gently and spin briefly (5 sec.) in table top centrifuge
3. Cycle the reactions using the cycling parameters outlined below:

| Segment | Cycles | Temperature | Time |
|---|---|---|---|
| 1 | 1 | 95° C. | 30 seconds |
| 2 | 18 | 95° C. | 30 seconds |
| | | 55° C. | 1 minute |
| | | 68° C. | 16 minutes |

Quality Control Analysis
1. To QC the amplification reactions, set up the following reactions in 96-well thin wall PCR plates or 0.2 ml thin wall PCR tubes:

| | |
|---|---|
| Mutagenesis reaction | 5 µl |
| Water | 4 µl |
| Sample loading buffer | 1 µl |
| Volume | 10 µl |

2. Load 10 µl onto a 1% agarose TAE gel with 0.5 µg/ml Ethidium Bromide. Use 1 kb plus DNA ladder as standard. Run the gel at 100V for 20-30 minutes in 1×TAE buffer.

Digest the Mutagenesis Reactions with Restriction Enzymes Appropriate for Cloning into Vector DNA—Example for DpnI Restriction Enzyme
1. Add 0.5 µl of the DpnI restriction enzyme (10 U/µl) directly to each reaction.
2. Mix gently and spin briefly (5 sec.) in a table top centrifuge
3. Incubate at 37° C. in PCR machines for 2 hours.
4. Transform 6 reaction mixtures from each of 96-well plate into XLI Blue Supercompetent cells. Store the rest of the reactions at −20° C.
5. Pre-chill 0.2 ml PCR tubes on ice. Warm SOC medium to 42° C.
6. Thaw the XLI Blue Supercompetent cells on ice. When thawed, gently mix and aliquot 50 µl of cells into each of the pre-chilled tubes.
7. Add 0.8 µl of beta-mercaptoethanol to each aliquot of cells. Incubate the cells on ice for 10 minutes, swirling gently every 2 minutes.
8. Add 2 µl of the reaction mixture to one aliquot of cells. Flick the tubes gently.
9. Incubate the tubes on cold blocks for 30 minutes.
10. Heat-pulse the tubes in a 42° C. water bath for 45 seconds.
11. Incubate the tubes on ice for 2 minutes
12. Add 100 µl of preheated SOC medium and incubate the tubes at 37° C. for 1 hour with shaking at 225-250 rpm.
13. Plate the entire transformation mixture on LB agar plates containing carbenicillin
14. Incubate the plates at 37° C. overnight.
15. Count colonies on plates and pick 12 colonies from each transformation reaction for miniprep and sequencing.

Large Scale Transformation
1. Thaw the XLI Blue Supercompetent cells on ice. Thaw 20 tubes of competent cells for 96 reactions. When thawed, add 4 µl of β-mercaptoethanol to each tube of 250 ul competent cells. Incubate the cells on ice for 10 minutes, swirling gently every 2 minutes.
2. Pre-chill 0.2 ml PCR tubes on ice. Warm SOC medium to 42° C.
3. Aliquot 50 µl of cells into each of the pre-chilled tubes.
4. Add 2 µl of the reaction mixture to one aliquot of cells. Flick the tubes gently.
5. Incubate the tubes on cold blocks for 30 minutes.
6. Heat-pulse the tubes in a 42° C. water bath for 45 seconds.
7. Incubate the tubes on ice for 2 minutes,
8. Add 100 µl of preheated SOC medium and incubate the tubes at 37° C. for 1 hour with shaking at 225-250 rpm.
9. Plate the entire transformation mixture on LB agar plates containing carbenicillin
10. Incubate the plates at 37° C. overnight.
11. Grow cells for in 96 well blocks for miniprep
12. Prepare miniprep DNA using QIAVac 96 kit following manufacture's protocol.

Example 3

Screening for Antibody Affinity Improvement

Transfection
One week before transfection, transfer 293F cells to monolayer culture in serum supplemented Dulbecco's Modified Eagle Medium (D-MEM). One day before transfection, plate $0.2 \times 10^5$ and $0.4 \times 10^5$ cells in 100 µl of serum supplemented D-MEM per transfection sample in 96 well formats.
1. For each transfection sample, prepare DNA-Lipofectamine complexes.
2. Dilute 0.2 µg of DNA in 50 µl Opti-MEM Reduced Serum Medium. Mix gently.
3. Dilute 0.125 µl Lipofectamine in 50 µl Opti-MEM Reduced Serum Medium. Mix gently and incubate for 5 min at room temperature.
4. Combine the diluted DNA with the diluted Lipofectamine. Mix gently and incubate for 20 mM at room temperature.
5. Add the 100 µl DNA-Lipofectamine complexes to each well containing cells and medium. Mix gently by rocking the plate back and forth.
6. Incubate the cells at 37° C. in a 5% $CO_2$ incubator.
7. Add 100 µl of serum supplemented D-MEM to each well after 6 hours. Incubate the cells at 37° C. in a 5% $CO_2$ incubator overnight.

8. Aspirate off medium in each well. Wash each well with 100 μl of 293 SFM II with 4 mM L-Glutamine. Add 100 μl of 293 SFM II with 4 mM L-Glutamine to each well.
9. Collect supernatant for ELISA at 96 hours after transfection.

Functional ELISA
1. Coat Nunc-Immuno Maxisorp 96 well plates with 100 μl of 2 μg/ml antigen in coating solution.
2. Cover plates with sealers and incubate overnight at 4 C.
3. Decant plates and tap out residue liquid.
4. Add 200 μl washing solution. Shake at 200 rpm for 5 min at room temperature.
5. Decant plates and tap out residue liquid.
6. Add 200 μl blocking solution. Shake at 200 rpm for 1 hour at room temperature.
7. Decant plates and tap out residue liquid.
8. Add duplicates of 100 μl/well of control antibody (2 μg/ml) in blocking solution to the plates.
9. Add duplicates of 100 μl of supernatant from transfection (SOP 5A) to the plates.
10. Shake at 200 rpm for one hour at room temperature.
11. Decant plates and tap out residual liquid.
12. Add 200 μl washing solution. Shake at 200 rpm for 5 min at room temperature.
13. Repeat step 11-12 3 times.
14. Add 100 μl of 1:5000 dilution of affinity purified goat anti-human antibody conjugate with HRP in blocking solution to each well.
15. Shake at 200 rpm for one hour at room temperature.
16. Decant plates and tap out residual liquid.
17. Add 200 μl washing solution. Shake at 200 rpm for 5 min at room temperature.
18. Repeat step 17-18 3 times.
19. Add 100 μl of Sigma TMB substrate to each well. Incubate at room temperature and check every 2-5 minutes.
20. Add 100 μl 1N HCl to stop the reaction.
21. Read at 450 nm Quantitation ELISA
1. Coat Nunc-Immuno Maxisorp 96 well plates with 100 μl of 10 μg/ml affinity-purified Fc-specific goat anti-human IgG in coating solution.
2. Cover plates with sealers and incubate overnight at 4 C.
3. Decant plates and tap out residue liquid.
4. Add 200 μl washing solution. Shake at 200 rpm for 5 min at room temperature.
5. Decant plates and tap out residue liquid.
6. Add 200 μl blocking solution. Shake at 200 rpm for 1 hour at room temperature.
7. Decant plates and tap out residue liquid.
8. Add duplicates of 100 μl/well of standardized concentration of purified human serum IgG in blocking solution to the plates.
9. Add duplicates of 100 μl of supernatant from transfection (SOP 5A) to the plates.
10. Shake at 200 rpm for one hour at room temperature.
11. Decant plates and tap out residual liquid.
12. Add 200 μl washing solution. Shake at 200 rpm for 5 min at room temperature.
13. Repeat step 11-12 3 times.
14. Add 100 μl of 1:5000 dilution of affinity purified goat anti-human antibody conjugate with HRP in blocking solution to each well.
15. Shake at 200 rpm for one hour at room temperature.
16. Decant plates and tap out residual liquid.
17. Add 200 μl washing solution. Shake at 200 rpm for 5 min at room temperature.
18. Repeat step 17-18 3 times.
19. Add 100 μl of Sigma TMB substrate to each well. Incubate at room temperature and check every 2-5 minutes.
20. Add 100 μl 1N HCl to stop the reaction.
21. Read at 450 nm Example 4

Generation and Screening of an Fc Codon Variant Library for Optimal Antibody Expression The present example provides methods for generating a Fc codon variant library and screening methods for obtaining Fc variants with optimized for improved expression in production host cells as compare to the parental form of Fc polypeptide.

A. Design and Construction of a Fc codon variant library

For each codon in the target area (in this case the Fc part of the human IgG1 molecule) a pair of degenerate primers (forward and reverse) is designed that includes the target codon and 20 bases on each side. The $3^{rd}$ position of the target codon (wobble position) contains mixed bases (Table 3) that allow the generation of all silent mutations at the target position using the same codon (example A). A second set of degenerate primer is designed for the same codon position if the corresponding amino acid can be encoded by another codon (example B). Corresponding forward and reverse degenerate primers are mixed 1:1, annealed to the template and extended to full length products by strand displacement using a thermostable DNA polymerase. Template is digested with DpnI and full length extension products are transformed into E. coli. Up to 12 colonies per mutagenesis reaction are sequenced. Sequence confirmed mutants are arrayed in 96 well plates and glycerol stocked. The glycerol stocks are used to miniprep plasmid DNA for transfection into mammalian cells and screening.

TABLE 3

Codes for degenerate bases in synthetic oligos

| Symbol | Mixed Base |
|---|---|
| R | A, G |
| Y | C, T |
| M | A, C |
| K | G, T |
| S | C, G |
| W | A, T |
| H | A, C, T |
| B | C, G, T |
| V | A, C, G |
| D | A, G, T |
| N | A, C, G, T |

Example A: target codon = CCC (proline)
→ forward primer: CCD, reverse primer: HGG
Example B; target codon = TCG (serine)
→ forward primer1: TCH, reverse primer1: DGA
→ forward primer2: AGY, reverse primer2: RCT
20 bases flanking the target codon are not shown. Total primer length: 43 bases.

B. Expression and ELISA Based Screening of Fc Codon Variant Library

Clones from the Fc codon variant library were transfected into a mammalian cell line. Full length IgGs were produced and secreted into the medium. Supernatants of expressed Fc codon variants were screened for IgG expression level higher than the parental clone using ELISA assay. The ELISA data was normalized with beta-galactosidase assay measuring the transfection efficiency. Top hits identified in the primary screen were re-transfected and re-screened three times to confirm the increased expression level.

I claim:

1. A method of evolution and expression of an antibody in a mammalian cell production host; the method comprising:
   a. evolving a template antibody to produce a set of mutant antibodies in a mammalian cell production host with antibody cell surface display, wherein the template antibody consists of an intact immunoglobulin molecule or a fragment of an immunoglobulin molecule and has a total of n amino acid residues, and said evolving comprises generating n-1 separate sets of mutant antibodies from the template antibody, each set comprising member antibodies having 19 different predetermined amino acid residues at a single predetermined position of the antibody, wherein each set of antibodies differs in the single predetermined position, and the number of different member antibodies generated is equivalent to [n−1]×19;
   b. screening the mutant antibodies for the at least one predetermined property, characteristic or activity;
   c. selecting an up-mutant antibody from the set of mutant antibodies based upon optimization of the at least one predetermined property, characteristic or activity compared to the template antibody; and
   d. expressing the up-mutant antibody in the same mammalian cell production host as was used in step (a).

2. The method of claim 1, wherein step (a) comprises steps of:
   a1. generating an anti-antigen antibody library in the mammalian cell production host with antibody cell surface display;
   a2. screening the library for the at least one predetermined property, characteristic or activity; and
   wherein the template antibody is selected from the library.

3. The method of claim 1 wherein the mammalian cell production host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, Chinese hamster ovary cells; R1 mouse embryonic cells; E14.1 mouse embryonic cells; H1 human embryonic cells; H9 human embryonic cells; PER C.6, human embryonic cells.

4. The method of claim 1, wherein the mammalian cell production host is CHO-S or HEK293.

5. The method of claim 1 wherein the screening step comprises fluorescence-activated cell sorting.

6. The method of claim 1 wherein the antibody is an antibody fragment selected from a heavy chain, light chain, variable domain, constant domain, hypervariable region, complementarity determining region 1, complementarity determining region 2, and complementarity determining region 3.

7. The method of claim 1, wherein the screening step (c) comprises:
   i. assaying each member antibody for at least one predetermined property, characteristic or activity;
   j. identifying any change in said property, characteristic or activity of the member antibody relative to the template antibody;
   k. creating a functional map wherein the functional map is used to identify positions and mutations in the mutant antibody which result in an up-mutant and/or a silent mutation compared to the template antibody.

8. The method of claim 1, wherein said evolving step comprises:
   i. subjecting a codon-containing polynucleotide encoding for said template antibody to polymerase-based amplification using a 64-fold degenerate oligonucleotide for each codon to be mutagenized, wherein each of said 64-fold degenerate oligonucleotides is comprised of a first homologous sequence and a degenerate N,N,N triplet sequence, so as to generate a set of progeny polynucleotides; and
   ii. subjecting said set of progeny polynucleotides to clonal amplification such that the mutant antibodies encoded by the progeny polynucleotides are expressed.

9. The method of claim 7 wherein the functional map is used to identify one or more of (a) positions and mutations which do not affect the activity of the mutant antibody compared to the template antibody; (b) fully mutable sites compared to the template antibody; and (c) positions and mutations which result in an up-mutant compared to the template antibody.

10. The method of claim 1 wherein the at least one predetermined property, characteristic or activity is selected from reduction of protein-protein aggregation, enhancement of protein stability, increased protein solubility, introduction of glycosylation sites, introduction of conjugation sites, reduction of immunogenicity, increase in antigen affinity, decrease in antigen affinity, change in binding affinity, change in immunogenicity, and enhancement of specificity.

11. The method of claim 2, wherein the anti-antigen antibody library is a humanized anti-antigen antibody library.

12. The method of claim 1 wherein the screening step comprises creating a functional map that is capable of being used to identify positions and mutations in the mutant antibodies which result in an up-mutant and/or a silent mutation compared to the template antibody.

13. The method of claim 3, wherein the mammalian cell production host is CHO cells.

14. The method of claim 1, further comprising a step of confirming by sequencing a presence of the predetermined amino acid residues at the single predetermined position in each member antibody.

* * * * *

UNITED STATES PATENT AND TRADEMARK OFFICE
CERTIFICATE OF CORRECTION

| | | |
|---|---|---|
| PATENT NO. | : 10,047,357 B2 | Page 1 of 1 |
| APPLICATION NO. | : 14/481564 | |
| DATED | : August 14, 2018 | |
| INVENTOR(S) | : Short | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this
Twenty-seventh Day of August, 2019

Andrei Iancu
*Director of the United States Patent and Trademark Office*